US010696792B2

(12) United States Patent
Odle et al.

(10) Patent No.: US 10,696,792 B2
(45) Date of Patent: Jun. 30, 2020

(54) TELECHELIC POLY(IMIDE) OLIGOMERS, METHODS OF MANUFACTURE, AND USES THEREOF

(71) Applicant: SABIC GLOBAL TECHNOLOGIES, B.V., Bergen Op Zoom (NL)

(72) Inventors: Roy Ray Odle, Mt. Vernon, IN (US); Guoliang Liu, Blacksburg, VA (US); Ke Cao, Blacksburg, VA (US); Timothy Edward Long, Blacksburg, VA (US); Joseph Michael Dennis, San Jose, CA (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/347,105

(22) PCT Filed: Nov. 16, 2017

(86) PCT No.: PCT/US2017/061986
§ 371 (c)(1),
(2) Date: May 2, 2019

(87) PCT Pub. No.: WO2018/094028
PCT Pub. Date: May 24, 2018

(65) Prior Publication Data
US 2019/0256658 A1 Aug. 22, 2019

Related U.S. Application Data

(60) Provisional application No. 62/422,628, filed on Nov. 16, 2016, provisional application No. 62/433,885, filed on Dec. 14, 2016.

(51) Int. Cl.
*C08G 73/10* (2006.01)
*C08K 5/3477* (2006.01)
(Continued)

(52) U.S. Cl.
CPC ......... *C08G 73/1017* (2013.01); *C08G 73/10* (2013.01); *C08G 73/1053* (2013.01);
(Continued)

(58) Field of Classification Search
None
See application file for complete search history.

(56) References Cited

U.S. PATENT DOCUMENTS 9,309,367 B2    4/2016  Xiao et al.
2016/0146978 A1  5/2016  Lee et al.

FOREIGN PATENT DOCUMENTS

CN    105037701 A   11/2015
WO    2016126102 A1  8/2016

OTHER PUBLICATIONS

Folmer et al (Supramolecular Polymer Materials: Chain Extension of Telechelic Polymers Using a Reactive Hydrogen-Bonding Synthon, Adv. Mater. 2000, 12, No. 12, pp. 874-878) (Year: 2000).*

(Continued)

*Primary Examiner* — Rachel Kahn
(74) *Attorney, Agent, or Firm* — Cantor Colburn LLP

(57) ABSTRACT

A ureido-pyrimidinone oligomer having the formula (I) wherein each Z' is independently the same or different, and is a substituted or unsubstituted straight or branched chain $C_{1-10}$ alkyl, each $R^1$ is independently the same or different, and is a substituted or unsubstituted straight or branched chain $C_{1-20}$ alkylene, substituted or unsubstituted $C_{2-20}$ alkenylene, substituted or unsubstituted $C_{3-8}$ cycloalkylene, or substituted or unsubstituted $C_{6-18}$ arylene, each V is independently the same or different, and is a substituted or unsubstituted tetravalent $C_{4-40}$ hydrocarbon group, each R is independently the same or different, and is a substituted or unsubstituted $C_{1-24}$ divalent hydrocarbon group; and n has an average value of 2 to 50, preferably 3 to 40, more preferably 5 to 30.

(Continued)

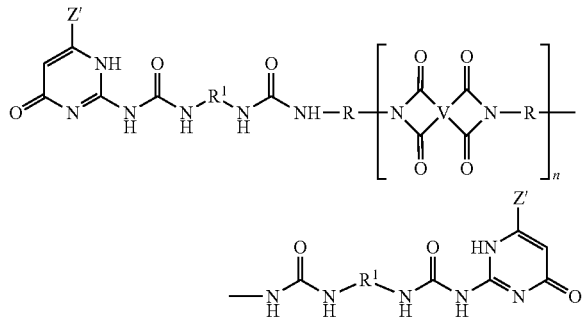

(I)

20 Claims, 13 Drawing Sheets

(51) Int. Cl.
*C08L 79/08* (2006.01)
*C07D 239/47* (2006.01)

(52) U.S. Cl.
CPC ........ *C08G 73/1078* (2013.01); *C08K 5/3477* (2013.01); *C08L 79/08* (2013.01); *C07D 239/47* (2013.01); *C08G 2105/06* (2013.01); *C08L 2203/12* (2013.01); *C08L 2203/14* (2013.01); *C08L 2203/16* (2013.01)

(56) References Cited

OTHER PUBLICATIONS

Cao et al., "Low-Molecular Weight, High-Mechanical-Strength, and Solution-Processable Telechelic Poly(ether imide) End-Capped with Ureidopyimidinone," American Chemical Society, Macromolecules, (2017), pp. 2016-2023.

International Search Report; International Application No. PCT/US2017/061986; International Filing Date—Nov. 16, 2017; dated Mar. 7, 2018; 5 pages.

Written Opinion of the International Searching Authority; International Application No. PCT/US2017/061986; International Filing Date—Nov. 16, 2017; dated Mar. 7, 2018; 6 pages.

Beijer et al., "Strong Dimerization of Ureidopyrimidones via Quadruple Hydrogen Bonding", Journal of the AmericanChemical Society, 1998, vol. 120, Issue 27, 6761-6769.

Wang Sumin et al, "Supramolecular assembly based on 2-uredio-4[1H]-pyrimidone", Chinese Science Bulletin, vol. 50, Issue 23, pp. 2565-2574, 2005, with English abstract translation.

Wang Sumin et al,"Supramolecular assembly based on 2-uredio-4[1H]-pyrimidone", Chinese Science Bulletin, vol. 51, No. 2, pp. 129-138, 2006.

Search Report for corresponding Chinese Patent Application No. 2017800685547, which is a national stage entry of PCT/US2017/061986, as dated Jan. 3, 2020.

* cited by examiner

TELECHELIC POLY(IMIDE) OLIGOMERS, METHODS OF MANUFACTURE, AND USES THEREOF

CROSS REFERENCE TO RELATED APPLICATIONS

This application is a National Stage application of PCT/US2017/061986, filed Nov. 16, 2017, which claims the benefit of U.S. Provisional Application No. 62/422,628, filed Nov. 16, 2016, and U.S. Provisional Application No. 62/433,885, filed Dec. 14, 2016, the entire contents of which are incorporated herein by reference.

BACKGROUND

Polyimide (PI), and in particular polyetherimide (PEI), are high-temperature engineering thermoplastic polymers with outstanding mechanical properties, thermal stability, and chemical resistance. Due to these excellent properties, PI, and in particular PEI, are widely used as matrix polymers, adhesives, and coatings in fields such as aerospace and advanced microelectronics. PEI polymers derived from 2,2-bis[4-(3,4-dicarboxyphenoxy)phenyl] propane dianhydride (BPADA) (such as the PEI polymer that is commercially available under the trade name ULTEM from SABIC) can be melt processed at 340° C. due to the flexible linkages in the PEI polymer backbone, for example, ether (—O—) and isopropylidene [—C(CH$_3$)$_2$—]. The viscosity of the high molecular weight polymers gives high viscosity which can lead to slower cycle time while injection molding or require higher temperatures than desired for the molding process. These drawbacks can be observed particularly in high molecular weight PI and PEI polymers.

Accordingly, there remains a need in the art for PI and PEI polymers that possess lower viscosity at processing temperatures and/or can be processed at lower temperatures. It would also be useful if the PI and PEI polymers could be processed by methods other than melt extrusion, for example methods such as solution-casting.

SUMMARY

A ureido-pyrimidinone oligomer has the formula unsubstituted C$_{1-24}$ divalent hydrocarbon group; and n has an average value of 2 to 50, preferably 3 to 40, more preferably 5 to 30.

Also disclosed are methods for the manufacture of the ureido-pyrimidinone oligomer.

Articles, including films, fibers, foams, and molded parts comprising the ureido-pyrimidinone oligomer are also disclosed.

BRIEF DESCRIPTION OF THE DRAWINGS

FIG. 4 is a graph of intensity (au) versus chemical shift (ppm) and shows $^1$H NMR spectra of (a) 8k-PEI-UPy, (b) 6k-PEI-UPy, (c) 4k-PEI-UPy, and (d) 2k-PEI-UPy in CDCl$_3$ according to an embodiment, wherein peak heights are normalized to peak a.

DETAILED DESCRIPTION

Figure 1:
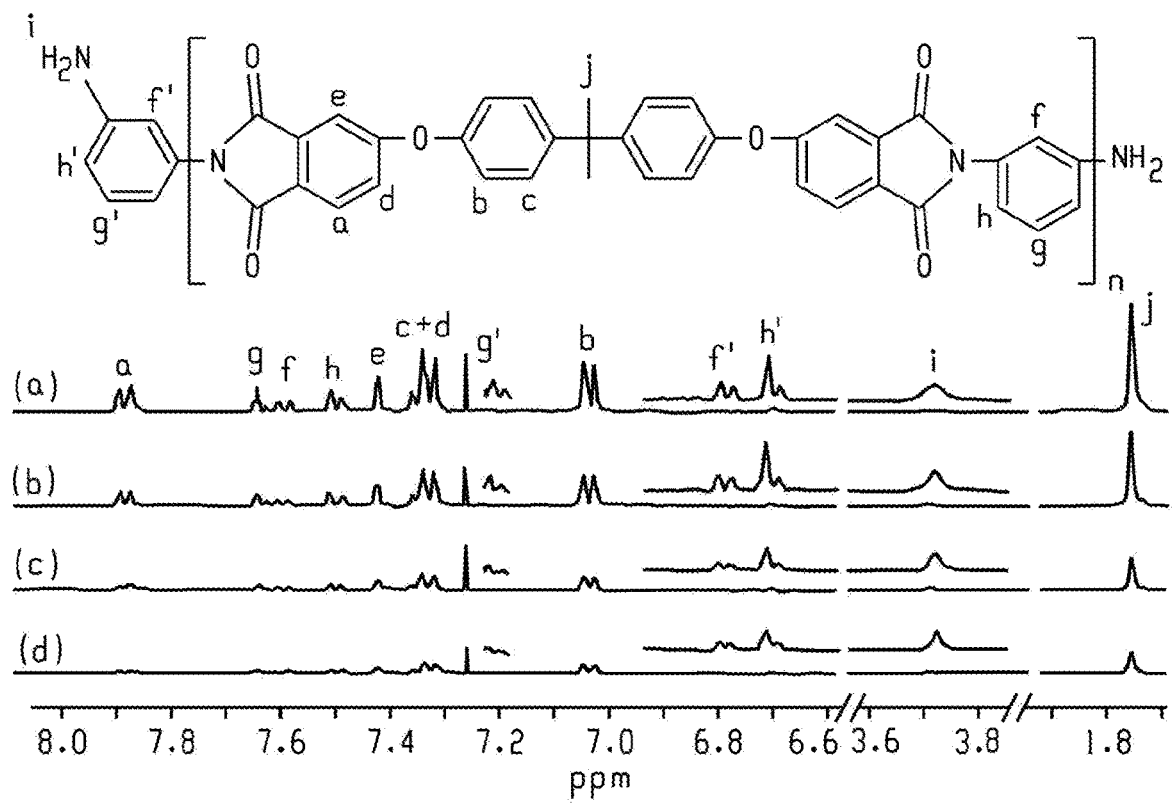
FIG. 1 is a graph of intensity (arbitrary units, au) versus chemical shift (parts per million, ppm), showing $^1$H NMR spectra of (a) 8k-PEI-NH$_2$, (b) 6k-PEI-NH$_2$, (c) 4k-PEI-NH$_2$, and (d) 2k-PEI-NH$_2$ in CDCl$_3$ according to an embodiment, where peak heights are normalized to peak i.

The inventors hereof have discovered PEI oligomers that can be used to form polyetherimides having reduced processing temperatures, and that can be prepared by melt processing or with alternative methods for making films, such as solution-casting. The PEI oligomers can be linked to larger molecular weight PEI polymers to form PEI polymers having interactive end-groups that can, for instance, provide interactive hydrogen-bonding. Such interactive groups also provide supramolecular PEI polymers with desirable mechanical properties.

The PEI oligomers are ureido-pyrimidinone (UPy)-terminated polyetherimide oligomers (PEI-UPy oligomers). Without being bound by theory, the PEI-UPy telechelic oligomers form linear supramolecular polymers, where the complimentary quadruple hydrogen bonds between two UPy groups have a dimerization constant of $K_{dim}=10^7$ M$^{-1}$ in CHCl$_3$. The UPy interactive end groups thus provide hydrogen-bonded supramolecular PEI polymers that can be used to improve the mechanical properties of polymers.

The PEI-UPy ureido-pyrimidinone oligomers are of formula (1).

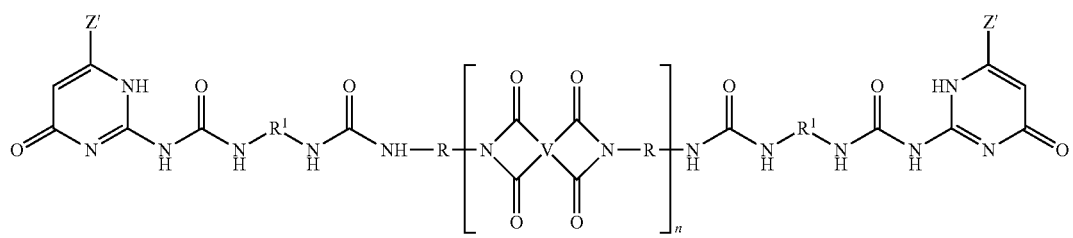

In formula (1), each Z' is independently a substituted or unsubstituted straight or branched chain C$_{1-10}$ alkyl, preferably a substituted or unsubstituted straight or branched chain C$_{1-6}$ alkyl, more preferably an unsubstituted C$_{1-3}$ alkyl, such as methyl.

In formula (1), each R$^1$ is independently a substituted or unsubstituted straight or branched chain C$_{1-20}$ alkylene, substituted or unsubstituted C$_{2-20}$ alkenylene, substituted or unsubstituted C$_{3-8}$ cycloalkylene, or substituted or unsubstituted C$_{6-18}$ arylene. In a preferred embodiment, each R$^1$ is independently a straight chain C$_{3-10}$ alkylene, preferably an unsubstituted straight chain C$_{3-10}$ alkylene, such as n-hexylene.

The polyimides of formula (1) comprise more than 1, for example 5 to 1000, or 5 to 500, or 10 to 100, structural units of formula (2)

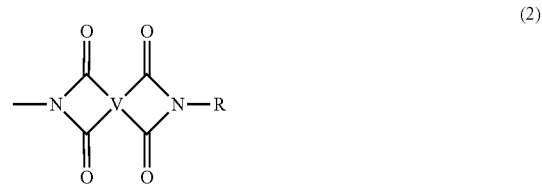

wherein each V is the same or different, and is a substituted or unsubstituted tetravalent C$_{4-40}$ hydrocarbon group, for example a substituted or unsubstituted C$_{6-20}$ aromatic hydrocarbon group, a substituted or unsubstituted, straight or branched chain, saturated or unsaturated C$_{2-20}$ aliphatic group, or a substituted or unsubstituted C$_{4-8}$ cycloaliphatic group, in particular a substituted or unsubstituted C$_{6-20}$ aromatic hydrocarbon group. Exemplary aromatic hydrocarbon groups include any of those of the formulas

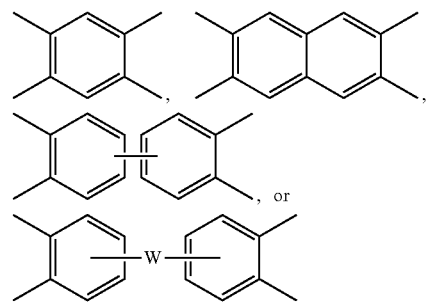

wherein W is —O—, —S—, —C(O)—, —SO$_2$—, —SO—, —P(R$^a$)(=O)— wherein R$^a$ is a C$_{1-8}$ alkyl or C$_{6-12}$ aryl, —C$_y$H$_{2y}$— wherein y is an integer from 1 to 5 or a halogenated derivative thereof (which includes perfluoroalkylene groups), or a group of the formula —O—Z—O— as described in formula (4) below.

Each R in formula (2) is the same or different, and is a substituted or unsubstituted C$_{1-24}$ divalent hydrocarbon group, such as a $C_{6-24}$ aromatic hydrocarbon group or a halogenated derivative thereof, a straight or branched chain $C_{1-20}$ alkylene group or a halogenated derivative thereof, a $C_{3-8}$ cycloalkylene group or halogenated derivative thereof, in particular a divalent group of formulas (3)

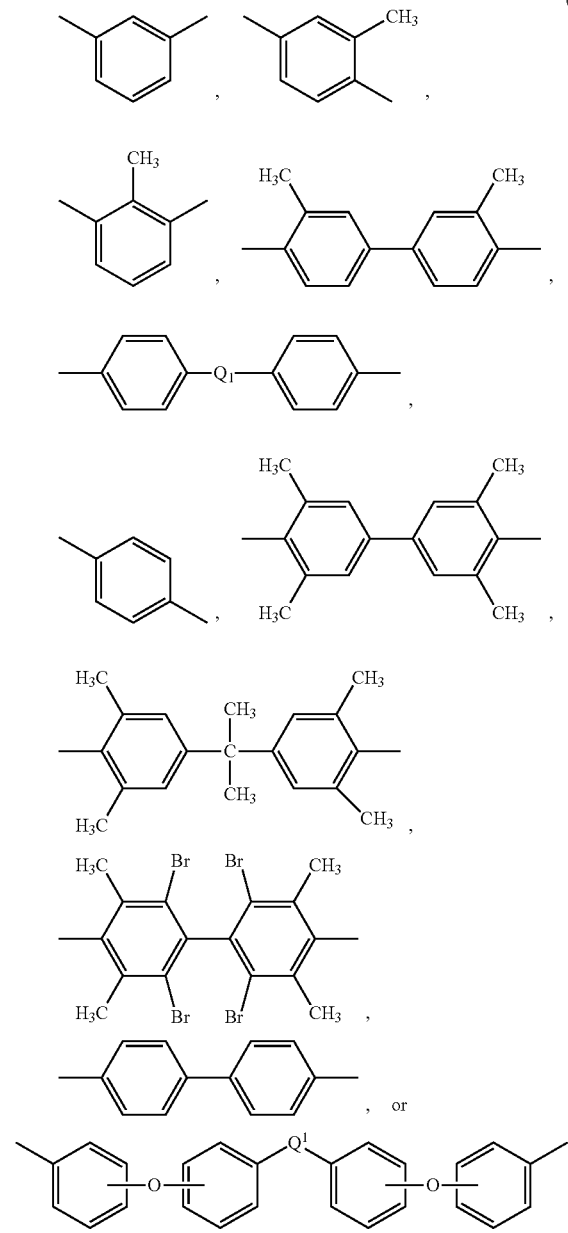

(3)

wherein $Q^1$ is —O—, —S—, —C(O)—, —SO$_2$—, —SO—, —P(R$^a$)(=O)— wherein R$^a$ is a $C_{1-8}$ alkyl or $C_{6-12}$ aryl, —C$_y$H$_{2y}$— wherein y is an integer from 1 to 5 or a halogenated derivative thereof (which includes perfluoroalkylene groups), or —(C$_6$H$_{10}$)$_z$— wherein z is an integer from 1 to 4. In an embodiment, R is m-phenylene, p-phenylene, or a diaryl sulfone.

Polyetherimides are a class of polyimides that comprise more than 1, for example 10 to 1000, or 10 to 500, structural units of formula (4)

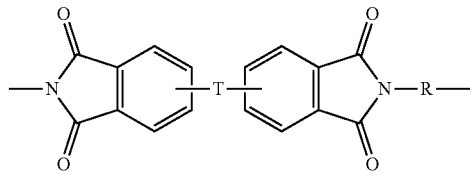

(4)

wherein each R is the same or different, and is as described in formula (2).

Further in formula (4), T is —O— or a group of the formula —O—Z—O— wherein the divalent bonds of the —O— or the —O—Z—O— group are in the 3,3', 3,4', 4,3', or the 4,4' positions. The group Z in —O—Z—O— of formula (4) is a substituted or unsubstituted divalent organic group, and can be an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, provided that the valence of Z is not exceeded. Exemplary groups Z include groups derived from a dihydroxy compound of formula (5)

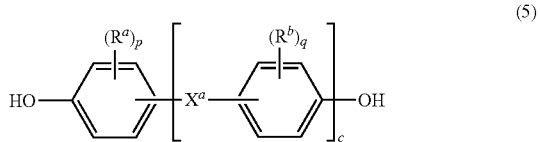

(5)

wherein R$^a$ and R$^b$ can be the same or different and are a halogen atom or a monovalent $C_{1-6}$ alkyl group, for example; p and q are each independently integers of 0 to 4; c is 0 to 4; and X$^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group X$^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ is organic bridging group. A specific example of a group Z is a divalent group of formula (5a)

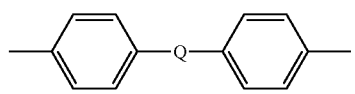

(5a)

wherein Q is —O—, —S—, —C(O)—, —SO$_2$—, —SO—, or —C$_y$H$_{2y}$— wherein y is an integer from 1 to 5 or a halogenated derivative thereof (including a perfluoroalkylene group). In a specific embodiment Z is a derived from bisphenol A, such that Q in formula (5a) is 2,2-isopropylidene.

In an embodiment in formula (4), R is m-phenylene or p-phenylene and T is —O—Z—O— wherein Z is a divalent group of formula (5a). Alternatively, R is m-phenylene or p-phenylene and T is —O—Z—O— wherein Z is a divalent group of formula (5a) and Q is 2,2-isopropylidene.

In some embodiments, the polyimide can be a copolymer, for example, a polyetherimide sulfone copolymer comprising structural units of formula (2) wherein at least 50 mole percent (mol %) of the R groups are of formula (3) wherein $Q^1$ is —$SO_2$— and the remaining R groups are independently p-phenylene or m-phenylene or a combination comprising at least one of the foregoing; and Z is 2,2'-(4-phenylene)isopropylidene.

Alternatively, the polyetherimide copolymer optionally comprises additional structural imide units, for example imide units of formula (2) wherein R and V are as described in formula (2), for example V is

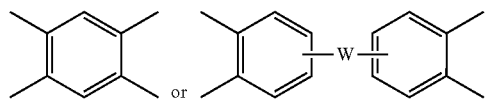

wherein W is a single bond, —O—, —S—, —C(O)—, —$SO_2$—, —SO—, —P($R^a$)(=O)— wherein $R^a$ is a $C_{1-8}$ alkyl or $C_{6-12}$ aryl, or —$C_yH_{2y}$— wherein y is an integer from 1 to 5 or a halogenated derivative thereof (which includes perfluoroalkylene groups). These additional structural imide units preferably comprise less than 20 mol % of the total number of units, and more preferably can be present in amounts of 0 to 10 mol % of the total number of units, or 0 to 5 mol % of the total number of units, or 0 to 2 mole % of the total number of units. In some embodiments, no additional imide units are present in the polyetherimide.

The polyimides can be prepared by any of the methods well known to those skilled in the art, including the reaction of an aromatic anhydride (6a) or bis(ether anhydride) of formula (6b)

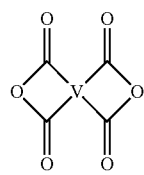
(6a)

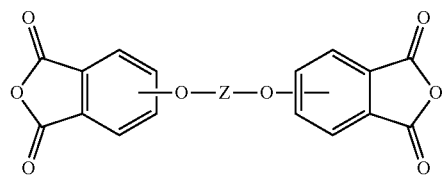
(6b)

or a chemical equivalent thereof, with an organic diamine of formula (7)

$$H_2N—R—NH_2 \quad (7)$$

wherein V, Z, and R are defined as described above. Copolymers of the polyetherimides can be manufactured using a combination of an aromatic bis(ether anhydride) of formula (6b) and a different bis(anhydride).

Illustrative examples of bis(ether anhydride)s include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl] propane dianhydride; 4,4'-bis(2,3-dicarboxyphenoxy)diphenyl ether dianhydride; 4,4'-bis(2,3-dicarboxyphenoxy) diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride, as well as various combinations thereof.

Examples of organic diamines include hexamethylenediamine, polymethylated 1,6-n-hexanediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2, 2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis (p-amino-t-butylphenyl) ether, bis(p-methyl-o-aminophenyl) benzene, bis(p-methyl-o-aminopentyl) benzene, 1, 3-diamino-4-isopropylbenzene, bis(4-aminophenyl) sulfide, bis-(4-aminophenyl) sulfone (also known as 4,4'-diaminodiphenyl sulfone (DDS)), and bis(4-aminophenyl) ether. Any regioisomer of the foregoing compounds can be used. Combinations of these compounds can also be used. In some embodiments, the organic diamine is m-phenylenediamine, p-phenylenediamine, 4,4'-diaminodiphenyl sulfone, or a combination comprising at least one of the foregoing.

The UPy-terminated oligomers can be synthesized by reaction of an amino-terminated oligomer of formula (8)

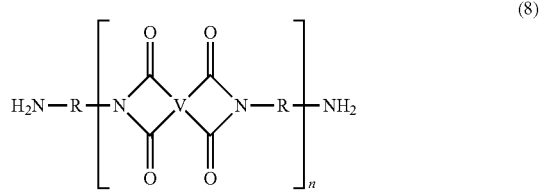
(8)

with an isocytosine of the formula (9)

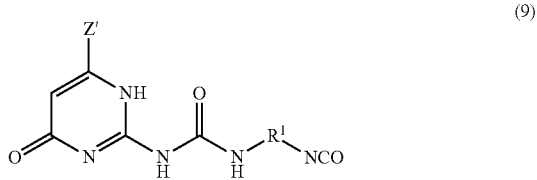

(9)

in the presence of a suitable catalyst, under conditions effective to produce the ureido-pyrimidinone oligomer.

Suitable catalysts include, but are not limited to, dibutyltin dilaurate and the like.

In a specific embodiment, the UPy-terminated oligomers are synthesized by reaction of an amino-terminated PEI of formula (10) with an isocytosine of the formula (9).

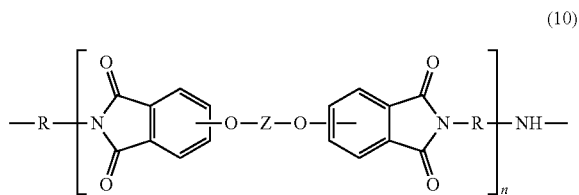

(10)

In an embodiment, the amino-terminated oligomer and the isocytosine are reacted at a mole ratio of 1:4 to 1:1, preferably 1:3 to 1:1.1, more preferably 1:2.5 to 1:1.5.

According to aspects of an embodiment, the reaction between the amino-terminated oligomer of formula (8) and the isocytosine of formula (9) includes reacting the amino-terminated oligomer and the isocytosine in a solvent at a first temperature for a first period of time to form a first intermediate mixture. Suitable solvents include chloroform and the like. In an embodiment, the first temperature is 40° C. to 90° C., preferably 50° C. to 75° C., more preferably 60° C. In an embodiment, the first period of time is 1 to 48 hours, preferably 12 to 36 hours. A catalyst is added to the intermediate mixture to form a second intermediate mixture, and the second intermediate mixture is heated at a second temperature to provide the ureido-pyrimidinone oligomer of formula (1). In an embodiment, the second temperature is 40° C. to 90° C., preferably 50° C. to 75° C., more preferably 60° C.

The polyimides and polyetherimides can have a melt index of 0.1 to 10 grams per minute (g/min), as measured by American Society for Testing Materials (ASTM) D1238 at 340° C. to 370° C., using a 6.7 kilogram (kg) weight. In some embodiments, the polyimides and polyetherimides can have a weight average molecular weight ($M_w$) of 1,000 to 150,000 grams/mole (g/mol), as measured by gel permeation chromatography (GPC), using polystyrene standards. In some embodiments, the polyimides and polyetherimides can have an $M_w$ of 10,000 to 80,000 g/mol. Such polyimides and polyetherimides can have an intrinsic viscosity greater than 0.2 deciliters per gram (dL/g), or, more specifically, 0.35 to 0.7 dL/g as measured in m-cresol at 25° C.

In some embodiments, proton nuclear magnetic resonance ($^1$H NMR) spectra of PEI-UPy had characteristic downfield signals from the UPy group at 9.9, 11.7, and 13.2 ppm as measured in deuterated chloroform.

In some embodiments, the polyimides and polyetherimides can have an intrinsic glass transition temperature ($T_g$) of greater than or equal to 180° C., preferably 180° C. to 280° C., or 200° C. to 250° C., as measured by differential scanning calorimetry (DSC).

The polyimides and polyetherimides can have a number average molecular weight ($M_n$) of 4,000 to 40,000 grams per mole (g/mol), preferably 4,000 to 12,000 g/mol, more preferably 5,000 to 10,000 g/mol, as measured by $^1$H NMR spectroscopy.

The polyimides and polyetherimides can have a Young's modulus of greater than or equal to $2.5 \times 10^3$ megapascals (MPa), preferably $3 \times 10^3$ MPa, as measured by standard methods. In some embodiments, the polyimides and polyetherimides can have a tensile strength of greater than or equal to 80 MPa, as measured by standard methods. In some embodiments, the polyimides and polyetherimides can have a maximum elongation of 2.5% to 5%, as measured by standard methods. Standard methods can include ASTM methods such as ASTM E111-04(2010), ASTM D638-14, or IPC-TM-650.

In additional embodiments, an article includes the UPy-terminated oligomers that are prepared using the methods described above. In some embodiments, the article is a film, a fiber, a foam, or a molded part. In some embodiments, the film is prepared by solution-casting the UPy-terminated oligomers that are prepared using the methods described above. In other embodiment, the film is prepared by melt processing the UPy-terminated oligomers that are prepared using the methods described above. Suitable temperatures for melt processing include, for example, 220° C. to 360° C., 230° C. to 350° C., 240° C. to 340° C., or 250° C. to 330° C. Similarly, a fiber, a foam, or a molded part can be prepared by solution-casting or melt processing using the UPy-terminated oligomers.

The above embodiments are further illustrated by the following examples, which are not intended to limit the claims.

EXAMPLES

Materials 2,2-Bis[4-(3,4-dicarboxyphenoxy)phenyl] propane dianhydride (BPADA) was supplied by SABIC and subjected to a heating-cooling cycle to remove any residual moisture before use.

Phthalic anhydride (PA) was provided by SABIC and used as received.

m-Phenylenediamine (mPD, 99%) was purchased from Sigma-Aldrich and purified by sublimation before use.

6-Methylisocytosine (MIS, 98%), hexamethylene diisocyanate (HMDI, 99%), and silica gel were purchased from Sigma-Aldrich and used as received.

o-Dichlorobenzene (oDCB) was purchased from Sigma-Aldrich. Chloroform ($CHCl_3$) was obtained from Spectrum Chemical. Methanol (MeOH) was obtained from Pharmco-AAPER. All deuterated solvents were purchased from Cambridge Isotope Laboratories, Inc. All solvents were used as received.

Analytical Methods

Proton nuclear magnetic resonance ($^1$H NMR) spectroscopy characterization was performed on a Varian Unity 400 at 399.98 MHz in deuterated chloroform.

Thermogravimetric analysis (TGA) was performed by heating the samples to 600° C. under a nitrogen flush of 60 mL/min on a TA instrument Q500 TGA.

Differential scanning calorimetry (DSC) was performed under a nitrogen flush of 50 mL/min at a heating rate of 10° C./min on a TA instruments Q1000 DSC, which was calibrated using indium (melting point, m.p.=156.60° C.) and zinc (m.p.=419.47° C.) standards. Glass transition temperature ($T_g$) was measured as the midpoint of the transition in the second heating ramp.

Polymers were dissolved in $CHCl_3$ and cast into a polytetrafluoroethylene Petri dish, followed by slow evaporation of the solvent and drying the film at 180° C. in vacuo.

Chloroform size exclusion chromatography (SEC) provided absolute molecular weights using a Waters 1515 Isocratic HPLC Pump and Waters 717plus Autosampler with Waters 2414 refractive index and Wyatt MiniDAWN MALLS detectors (flow rate 1.0 mL $min^{-1}$).

Tensile testing was performed on a 5500R Instron universal testing at a cross-head speed of 5 mm $min^{-1}$. The tensile strength, maximum elongation, and Young's moduli are reported based on an average of five specimens.

Synthesis of $PEI-NH_2$

Scheme 1 illustrates the general synthetic procedure and reaction conditions for the synthesis of an amine-terminated polyetherimide from BPADA and mPD with a stoichiometric imbalance.

gomer, as confirmed by $^1H$ NMR spectroscopy (FIG. 1). The amine end-groups allowed quantification of the degree of polymerization using $^1H$ NMR spectroscopy, which further afforded the calculation of $M_n$ for several $PEI-NH_2$ oligomers (Table 1). An exemplary procedure for calculating the $M_n$ of an amine-terminated PEI oligomer having a target molecular weight of 2,000 g/mol ($2k-PEI-NH_2$) is described in further detail below.

The calculated molecular weights of several $PEI-NH_2$ oligomers were further confirmed by determining the molecular weights of similar PA-terminated PEI oligomers using SEC (Table 1), which were synthesized by end-capping a $PEI-NH_2$ oligomer with PA. An exemplary procedure for calculating the molecular weights of the PA-terminated PEI oligomers using SEC is described in further detail below.

TABLE 1

| Sample | Theoretical $M_n$ (kDa) | NMR $M_n$ (kDa) | SEC $M_n$ (kDa)* | $T_{d,5\%}$ (° C.) | $T_g$ (° C.) |
|---|---|---|---|---|---|
| $8k-PEI-NH_2$ | 7.8 | 8.0 | 8.4 | 537 | 205 |
| $6k-PEI-NH_2$ | 6.0 | 5.6 | 7.1 | 534 | 199 |
| $4k-PEI-NH_2$ | 4.3 | 4.5 | 5.8 | 533 | 195 |
| $2k-PEI-NH_2$ | 2.5 | 3.1 | 3.1 | 528 | 185 |

*$M_n$ determined from SEC and corrected by the $M_n$ difference between $PEI-NH_2$ and PA-terminated $PEI-NH_2$.

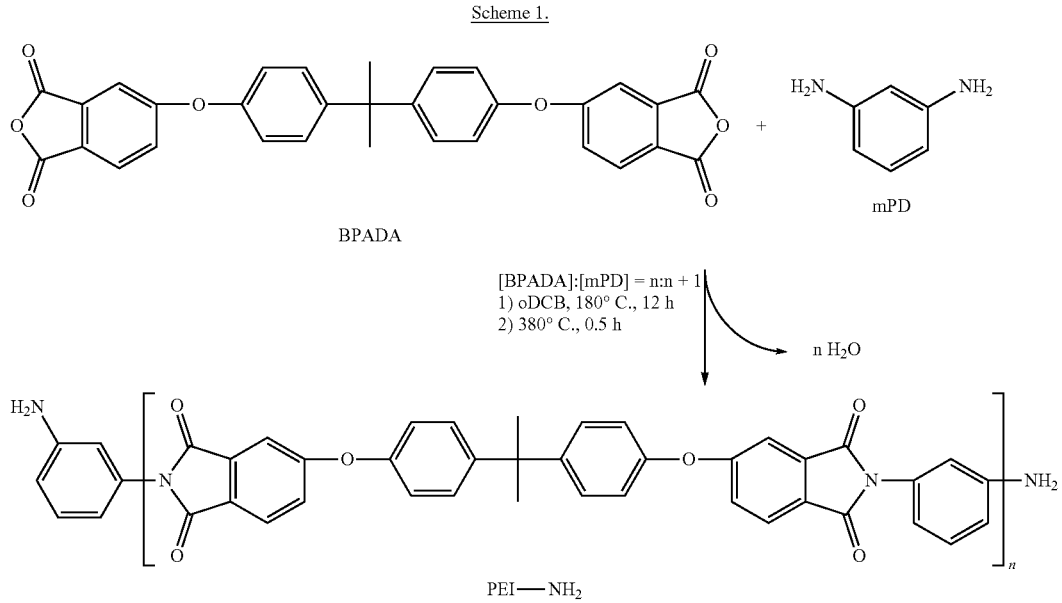

Scheme 1.

An exemplary synthesis of a $PEI-NH_2$ oligomer having an average molecular weight ($M_n$) of 2,500 grams per mole (g/mol) is as follows. A three-neck 500 milliliter (mL) round-bottomed flask, equipped with an overhead stirring-rod, a Dean-Stark trap, and a nitrogen inlet, was charged with BPADA (16.800 grams (g), 32.28 millimoles (mmol)), mPD (4.363 g, 40.35 mmol), and 60 mL oDCB, and then purged with $N_2$. Subsequently, the slurry was heated at 180° C. and stirred for 12 hours (h), and then heated at 380° C. in a metal bath for 30 minutes (min). The entire reaction was conducted under a constant stream of $N_2$. The oligomer was recovered by dissolution in $CHCl_3$ and precipitation into MeOH. The precipitate was filtered and washed with MeOH three times, and dried in vacuo at 180° C. for 8 h.

Figure 2:
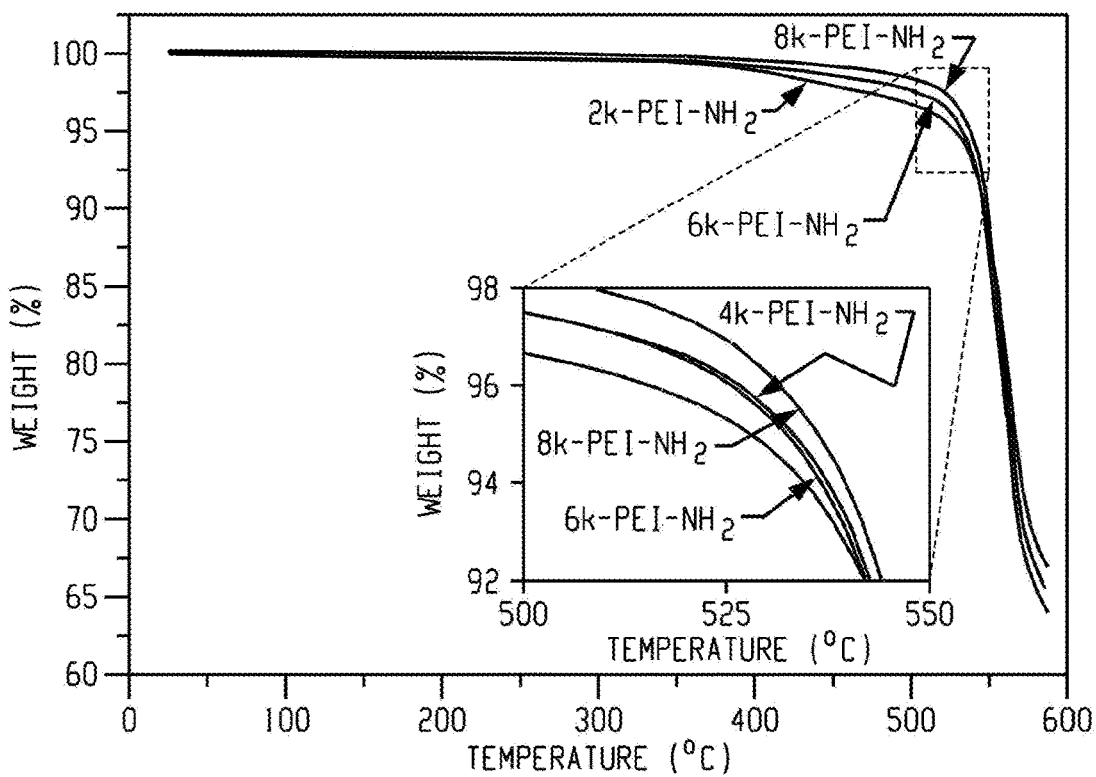
FIG. 2 is a graph of weight (percent, %) versus temperature (° C.) and shows thermogravimetric analysis (TGA) thermograms illustrating the thermal stability of the PEI-NH$_2$ oligomers according to an embodiment.

The use of a stoichiometric excess of mPD generated the $PEI-NH_2$ oligomer, an amine-terminated polyetherimide oli- TGA and DSC were used to analyze the thermal properties of the $PEI-NH_2$ oligomers. TGA revealed the high thermal stability of the $PEI-NH_2$ oligomers. The $PEI-NH_2$ oligomers were degraded through a single degradation step in the range of 400 to 600° C. (FIG. 2; the inlet shows the enlarged curves around 5% weight loss.). The results show good thermal stability up to 500° C.

To establish a relationship between $M_n$ and the thermal stability of the PEI-NH$_2$ oligomers, the degradation temperatures for a 5% weigh loss ($T_{d,5\%}$) values of the PEI-NH$_2$ oligomers were collected (Table 1). Although $T_{d,5\%}$ increased slightly with a decreasing $M_n$, the PEI-NH$_2$ oligomers showed outstanding thermal stability at temperatures greater than 520° C., which is attributed to the strong imide rings in the PEI backbones. TGA traces of 6k-PEI-NH$_2$ and 4k-PEI-NH$_2$ oligomers overlapped to some extent (FIG. 2, inset), probably due to their close proximity of molecular weight or experimental error.

Figure 3A:
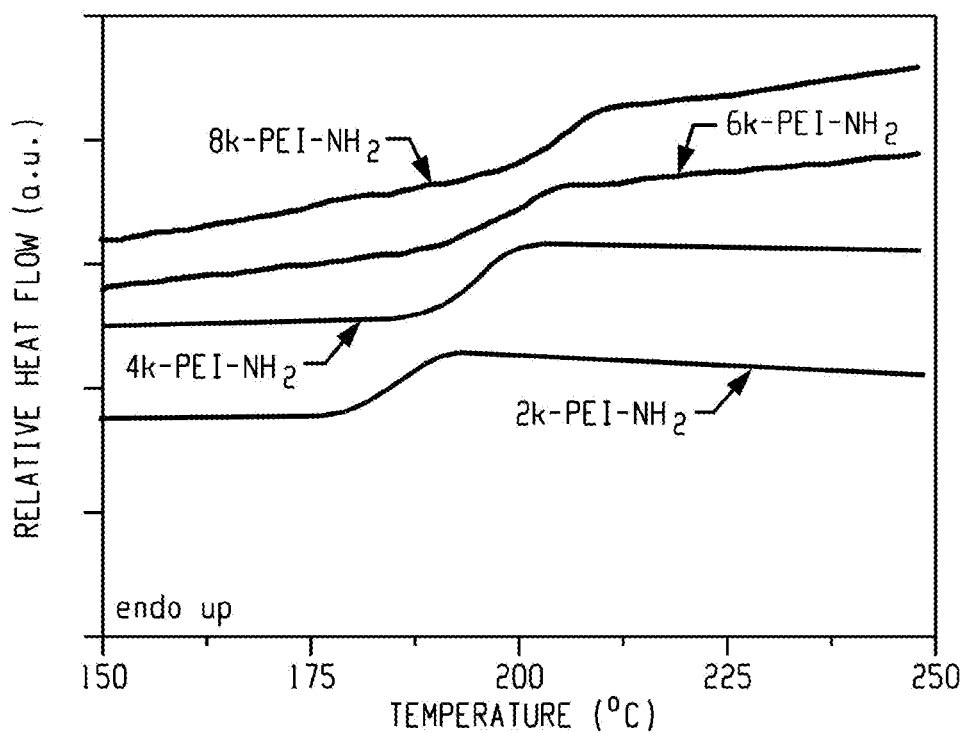
FIG. 3A is a graph of relative heat flow (au) versus temperature (° C.) and shows differential scanning calorimetry (DSC) traces of the PEI-NH$_2$ oligomers according to an embodiment.
Figure 3B:
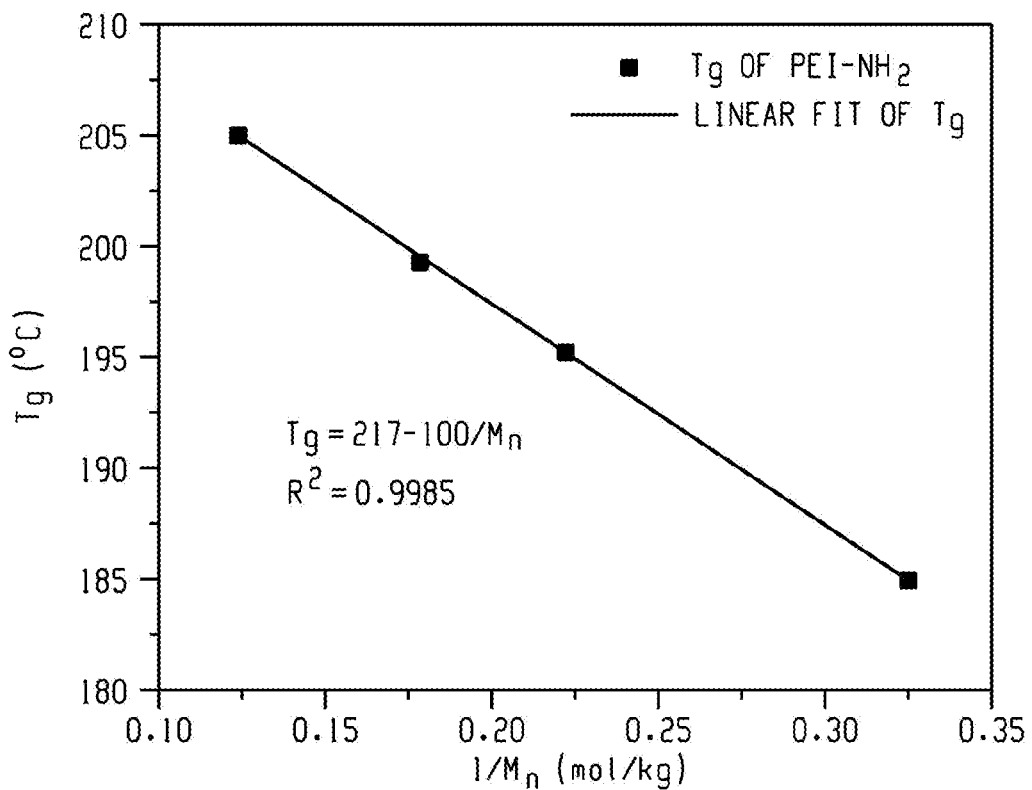
FIG. 3B is a graph of glass transition temperature (Tg, ° C.) versus 1/M$_n$ (moles per kilogram, mol/kg) and shows data obtained using the Flory-Fox equation for the PEI-NH$_2$ series according to an embodiment.

DSC was used to determine the glass transition temperatures of the PEI-NH$_2$ oligomers (FIG. 3A). As observed in the DSC traces, $T_g$ increased with $M_n$, and could be fitted well with the empirical Flory-Fox equation (Equation 1).

$$T_g = T_{g,\infty} - \frac{K}{M_n} \qquad \text{Eq. (1)}$$

with $R^2$=0.9985 and K is an empirical parameter related to the free volume of the polymer samples (FIG. 3b). The linear fitting generated an intrinsic glass transition temperature ($T_g$, ∞) of 217° C., which is in excellent agreement with the $T_g$ of commercially available high molecular weight PEI polymers (ULTEM 1000 and ULTEM 1010, $T_g$=217° C., from SABIC).

Synthesis of UPy-Synthon

UPy-synthon was synthesized following a method described in a previous report (Keizer et al., Macromolecules, vol. 36, 5602-06 (2003)) as shown in Scheme 2.

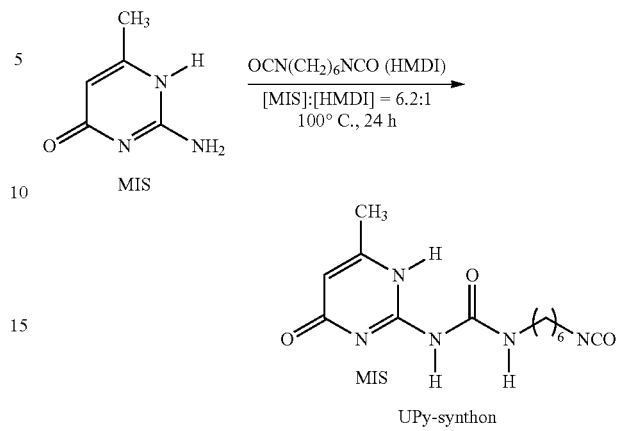

Scheme 2.

A suspension of MIS (12 g, 95.92 mmol) and a 6.2-fold excess of HMDI (100 g, 595 mmol) was stirred at 100° C. for 24 h. The white product was precipitated in hexanes, washed with hexanes three times, and then filtered and dried at 40° C. in vacuo. $^1$H NMR (400 MHz, CDCl$_3$, 6): 13.1 ppm (s, 1H, —NH—C(CH$_3$)═ (a)), 11.9 ppm (s, 1H, —NH—CO—NH—CH$_2$— (b)), 10.2 ppm (s, 1H, —NH—CO—NH—CH$_2$— (c)), 5.8 ppm (s, 1H, —CH═C(CH$_3$) (d)), 3.3 ppm (m, 4H, —NH—CO—NH—CH$_2$—, —CH$_2$NCO— (e)), 2.2 ppm (s, 3H, —NHC(CH$_3$)═CH—CO— (f)), 1.3-1.7 ppm (m, 8H, —(CH$_2$)$_4$— (g)). ESI-MS calcd: M=293.1 g/mol; found: m/z 294.2 [M+H]$^+$, 316.1 [M+Na]$^+$, 587.3 [2M+H]$^+$, 609.3 [2M+Na]$^+$.

Synthesis of UPy-Terminated Polyetherimide (PEI-UPy)

PEI-UPy was prepared by reacting PEI-NH$_2$ oligomer with an excess of the UPy-synthon in CHCl$_3$ as shown in Scheme 3.

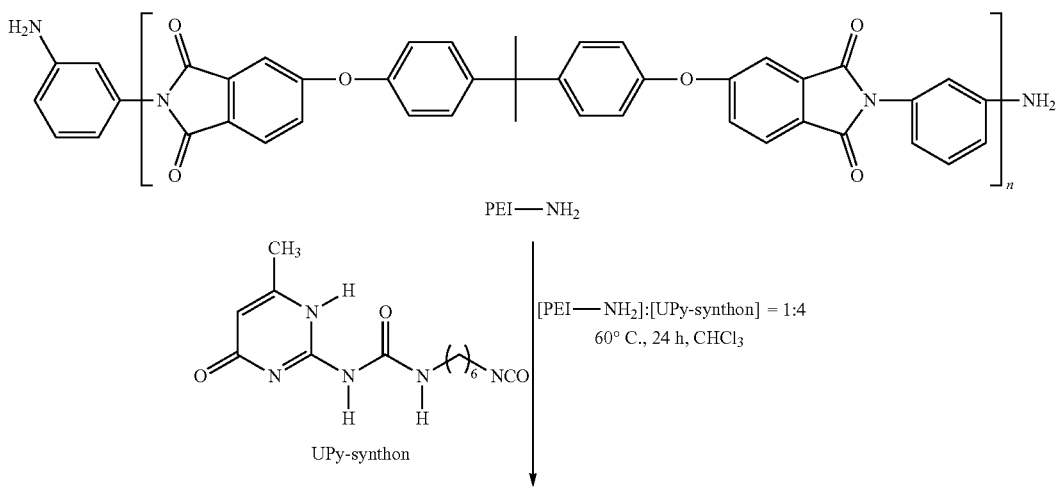

Scheme 3.

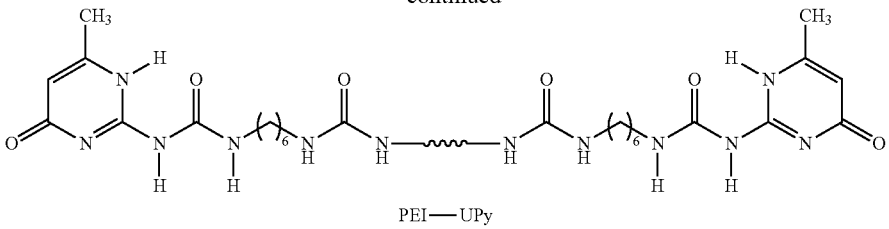

∿∿∿: PEI backbone

The synthesis is as follows. A flamed dried, $N_2$ purged 100 mL round-bottomed flask was charged with PEI-$NH_2$ ($M_n$=3,100 g/mol, 3.100 g, 1 mmol), UPy-synthon (1.173 g, 4 mmol), and $CHCl_3$ (60 mL), and then purged with $N_2$. The reaction mixture was stirred at 60° C. for 24 h. Subsequently, 2.346 g of silica gel and 0.5 mL 3 wt % dibutyltin dilaurate in THF (3 wt %) were added to the mixture and allowed to react at 60° C. for 1 h. The suspension was diluted by 120 mL $CHCl_3$ and filtered through a plug of diatomaceous Earth. The filtrate was precipitated in MeOH. The precipitate was filtered and washed with MeOH three times and dried in vacuo at 100° C. for 24 h.

Figure 4:
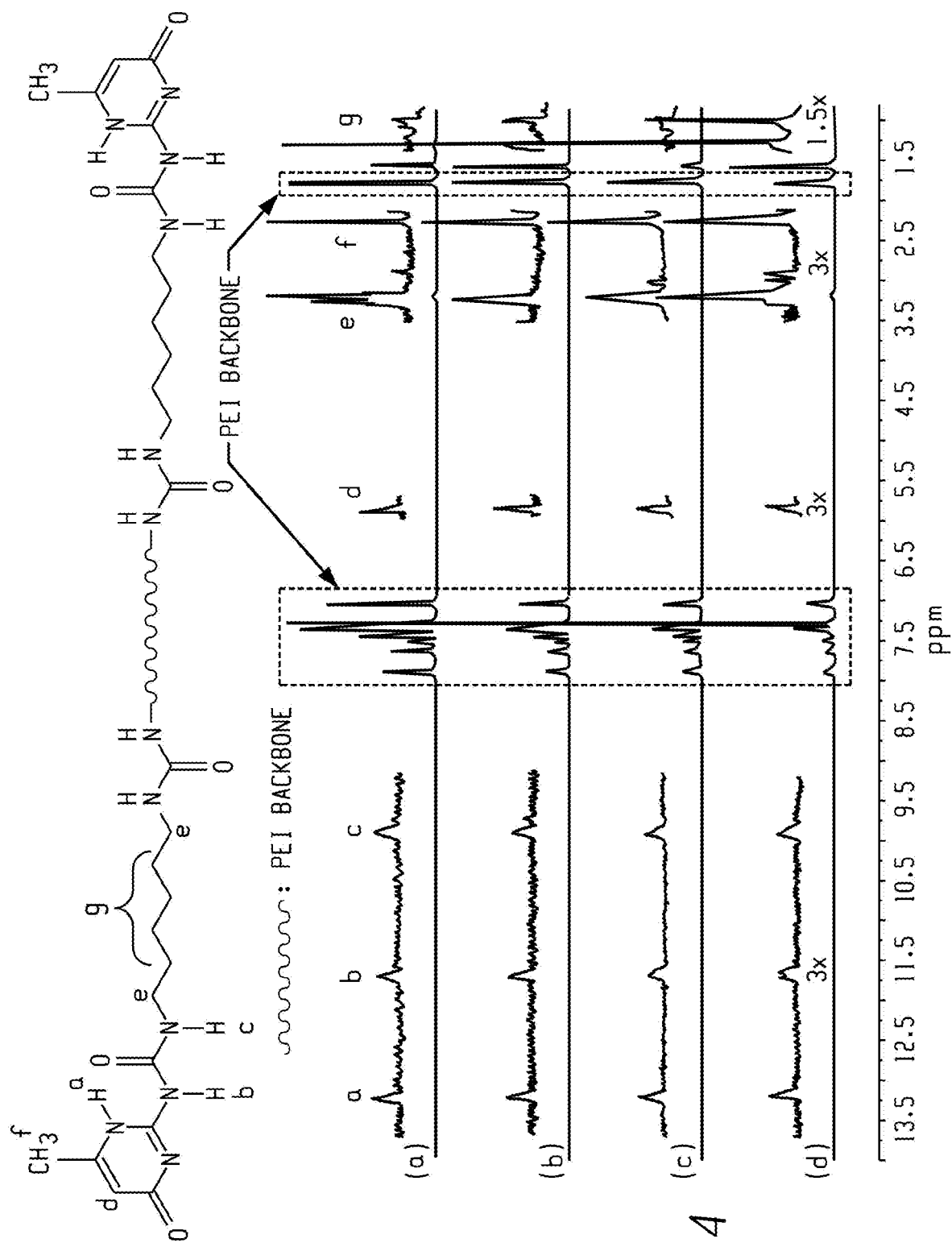

Reacting the PEI-$NH_2$ oligomer with the UPy-synthon at a ratio of [$NH_2$]:[NCO]=1:2 provided maximum transformation of the PEI-$NH_2$ oligomer into to PEI-UPy oligomer. The viscosity of the reaction mixture increased significantly compared to the precursors. The $^1$H NMR spectra of the PEI-UPy oligomers had characteristic downfield signals of the UPy group (9.9, 11.7, and 13.2 ppm), confirming the successful incorporation of UPy moieties (FIG. 4). However, the three peaks shifted slightly from original peak positions in the UPy-synthon (data not shown). Since there was a stoichiometric excess of the UPy-synthon in the reaction, adding silica gel removed the un-reacted UPy-synthon in the reactor, as confirmed by $^1$H NMR spectroscopy (data not shown). Although the reaction conditions were optimized and an excess of the UPy-synthon was maintained in the reaction, the conversion of the PEI-$NH_2$ oligomers to the PEI-UPy oligomers was incomplete, as suggested by a minor amine peak at 3.78 ppm (data not shown). The incomplete conversion of the PEI-$NH_2$ oligomers to the PEI-UPy oligomers is probably due to the high viscosity of the reaction mixtures. To calculate the conversion, PA was added to react with the residual PEI-$NH_2$ oligomers. The calculation based on the formation of PA-capped PEI oligomers suggested that the conversions from —$NH_2$ to —UPy for the PEI-$NH_2$ oligomers was greater than 90%, showing that the incorporation of the UPy groups into the PEI backbone reached an acceptable level by reacting the PEI-$NH_2$ oligomers with the UPy-synthon.

Figure 5:
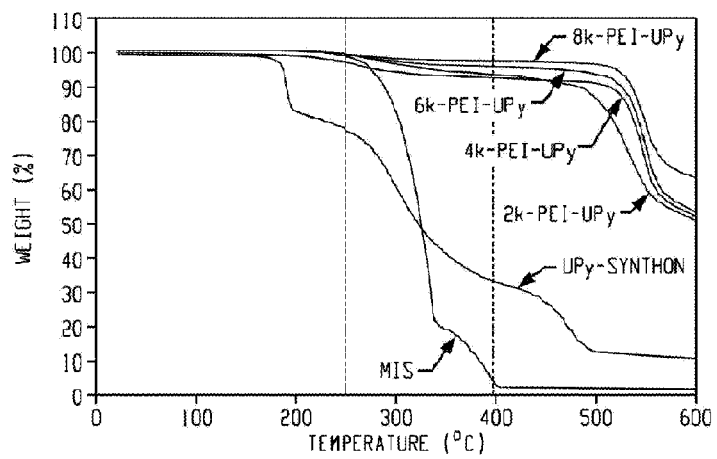
FIG. 5 is a graph of weight (%) versus temperature (° C.) and shows TGA thermograms exhibiting the thermal stability of the PEI-UPy polymers, the UPy-synthon, and 6-methylisocytosine (MIS) according to an embodiment.

Thermal analysis of the PEI-UPy oligomers showed a two-stage weight loss when measured using TGA (FIG. 5). The first stage occurred at about 240° C. due to the decomposition of 6-methylisocytosine (MIS) moieties in PEI-UPy oligomers. This was confirmed by comparing the onset degradation temperatures of PEI-UPy oligomers and pure MIS (240° C.). In addition, the amount (%) of weight loss from the PEI-UPy oligomers during the first stage of thermal degradation matched with the theoretical amount of MIS (%) that was incorporated in the PEI-UPy oligomers (Table 2).

TABLE 2

| Sample | UPy-functionalization (%) | Theoretical MIS (%) | Wt loss at 400° C. (%) | $T_g$ (° C.) |
|---|---|---|---|---|
| 8k-PEI-UPy | 82 | 2.9 | 2.9 | 215 |
| 6k-PEI-UPy | 83 | 4.0 | 4.5 | 210 |
| 4k-PEI-UPy | 87 | 4.9 | 6.8 | 208 |
| 2k-PEI-UPy | 88 | 6.8 | 6.7 | 205 |

The degradation temperature at the first stage was greater than that of the UPy-synthon, indicating that the UPy-synthon "tail" in the PEI-UPy polymers did not degrade at the degradation temperature of the UPy-synthon. The higher degradation temperature of the UPy-synthon "tail" is attributed to the change of molecular conformation of UPy-synthon. After reacting with the PEI-$NH_2$ oligomers, the UPy-synthon "tail" is mounted to the PEI backbone and loses some chain flexibility; while in the UPy-synthon, the "tail" is flexible and degrades at a lower temperature. The weight loss at the second stage was from the degradation of the PEI backbones, similar to that of the PEI-$NH_2$ oligomers.

Figure 6:
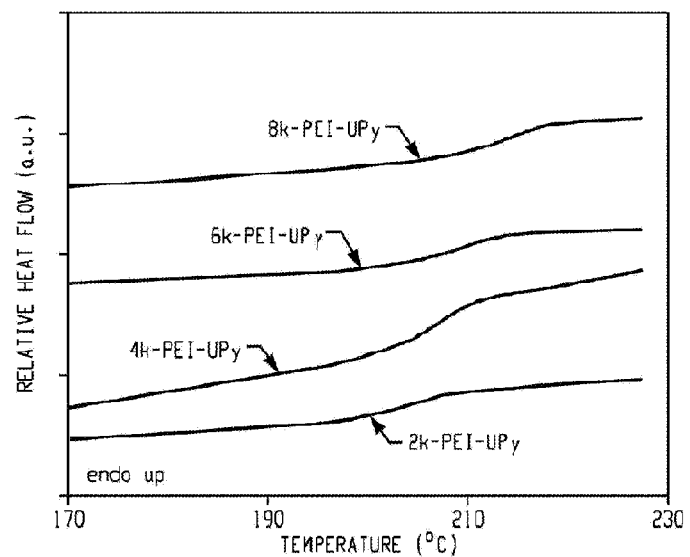
FIG. 6 is a graph of relative heat flow (au) versus temperature (° C.) and shows DSC traces of the PEI-UPy series of the Examples.

DSC measurements revealed significant increases in $T_g$ after incorporating the UPy end-groups into the PEI backbone (FIG. 6). The $T_g$ of the PEI increased by 10, 11, 13 and 20° C. for 8k-, 6k-, 4k-, and 2k-PEI-UPy oligomers, respectively (Table 2). Furthermore, the changes in $T_g$ are more significant for oligomers with lower molecular weights, which is in agreement with the previous study on UPy-telechelic polycaprolactones. In UPy-functionalized poly (styrene) and poly(isoprene) melts, H-bonded UPy end-groups could still exist even at elevated temperatures. Similarly, UPy-functionalized PEI polymers had stronger chain interactions than the PEI-$NH_2$ oligomers did at temperatures greater than the dissociation temperature of UPy dimers. Therefore, we observed an increased $T_g$ after incorporating UPy end-groups into the PEI-$NH_2$ oligomers. This phenomenon can be attributed to the formation of a urea bond after incorporation of UPy end groups.

To test the mechanical properties of the PEI-$NH_2$ oligomers and the PEI-UPy oligomers, solution-cast films were made using $CHCl_3$ as the solvent. Among the oligomers, 8k-PEI-UPy and 8k-PEI-$NH_2$ formed intact films (data not shown). The film-forming ability of the PEI-UPy oligomers seemed to mainly depended on the molecular weight rather than on the end-groups, in agreement with the understanding that high molecular weight dictates the physical properties of PEI polymers. The inability to form films prevented comparing the mechanical properties of the PEI-$NH_2$ oligomers and the PEI-UPy oligomers having an $M_n$ less than 6 kDa.

The comparison between 8k-PEI-UPy and 8k-PEI-$NH_2$ oligomers highlighted the advanced mechanical properties achieved by UPy functionalization. Although the 8k-PEI-NH$_2$ and 8k-PEI-UPy oligomers showed film-forming ability, the solution-cast films of 8k-PEI-NH$_2$ oligomer were fragile and could not be cut into intact dumbbell structures. In contrast, solution-cast films of 8k-PEI-UPy oligomer could be cut into dumbbell shaped structures, and showed great flexibility (1800 without breaking when bent by hand). The sharp difference in film flexibility shows that incorporation of the UPy end-groups improved significantly the mechanical properties of the 8k-PEI-UPy oligomer relative to the mechanical properties of the 8k-PEI-NH$_2$ oligomer.

Figure 7A:
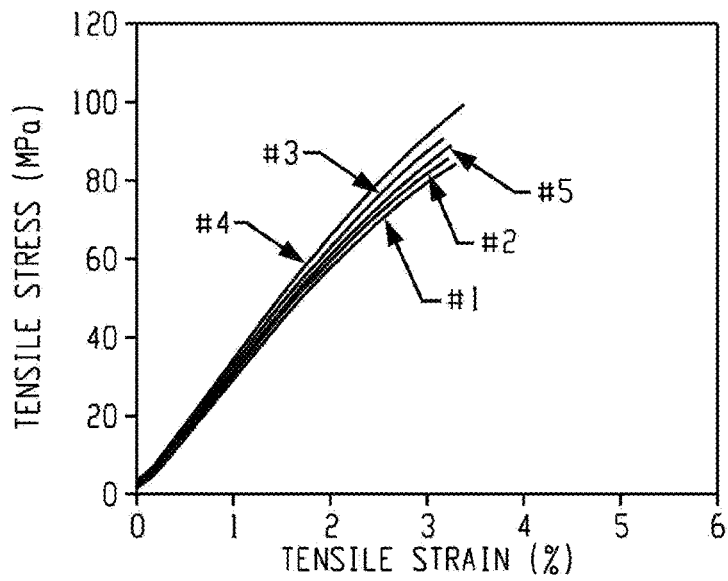
FIGS. 7A, 7B, and 7C are graphs of tensile stress (megapascals, MPa) versus tensile strain (%) and show the stress-strain curves obtained from tensile tests of (a) a film made from 8k-PEI-UPy, (b) a film made from a commercially available PEI polymer, and (c) a film made from a second commercially available PEI polymer.
Figure 7B:
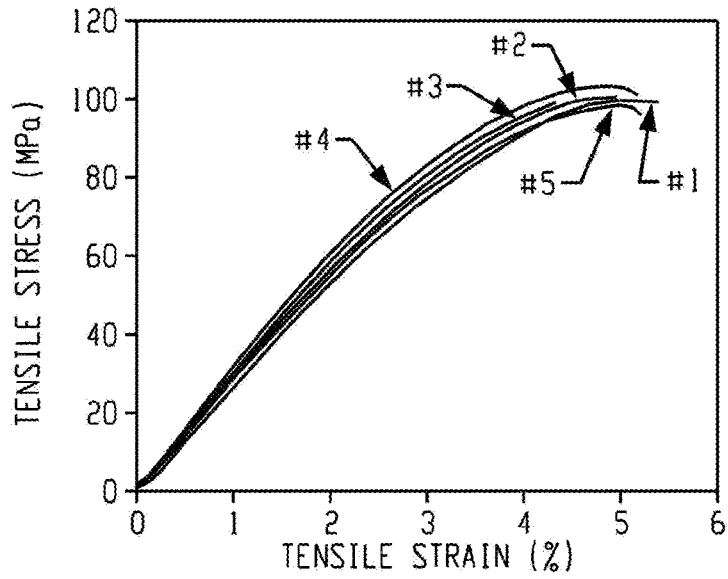
Figure 7C:
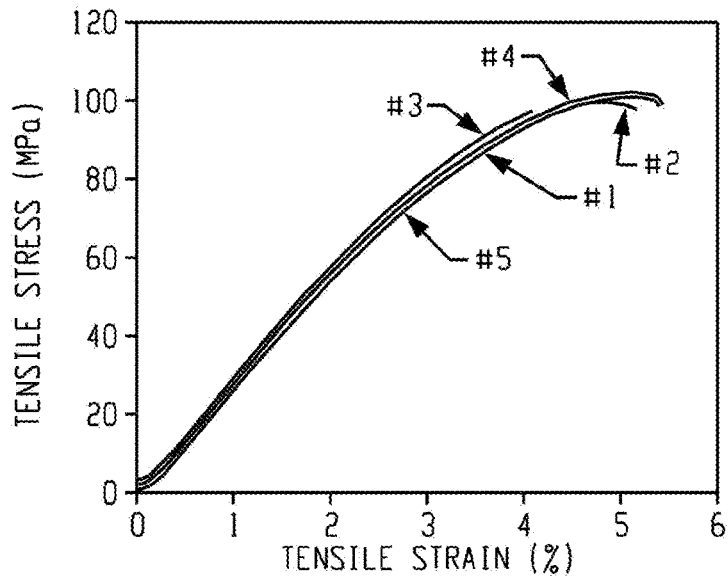

The mechanical properties of the solution-cast 8k-PEI-UPy oligomer film and commercially available PEI polymers (ULTEM 1000 and ULTEM 1010) are shown in FIG. 7. Surprisingly, the 8k-PEI-UPy oligomer film (FIG. 7A), with a molecular weight of 8,700 g/mol (calculated by assuming full conversion from 8k-PEI-NH$_2$ to 8k-PEI-UPy), showed a greater Young's modulus than ULTEM 1000 (FIG. 7B) ($M_n$=24,500 g/mol, determined by SEC) and ULTEM 1010 (FIG. 7C) ($M_n$=16,900 g/mol, determined by SEC), while its tensile strength and maximum elongation were comparable (Table 3). These results showed that incorporation of UPy end-groups not only improved the mechanical properties of lower molecular weight PEIs, but also provided mechanical properties (e.g., Young's modulus) that are comparable to, or even better than, higher molecular weight PEIs.

TABLE 3

| Sample | Tensile strength (MPa) | Max elongation (%) | Young's modulus (MPa) |
|---|---|---|---|
| 8k-PEI-UPy | 87.2 ± 10.8 | 3.10 ± 0.39 | (3.20 ± 0.14) × 10$^3$ |
| ULTEM 1000 | 99.0 ± 1.3 | 5.02 ± 0.40 | (2.94 ± 0.12) × 10$^3$ |
| ULTEM 1010 | 98.8 ± 1.1 | 4.98 ± 0.54 | (2.79 ± 0.09) × 10$^3$ |

In summary, after functionalization with UPy end-group, PEI oligomers with an $M_n$ as low as about 8 kDa can be solution-cast to form films. Tensile tests revealed that 8k-PEI-UPy oligomer had outstanding mechanical properties comparable to those of ULTEM 1000 and ULTEM 1010 from SABIC. The tensile strength, maximum elongation, and Young's modulus of the 8k-PEI-UPy oligomer were 87.2±10.8 MPa, 3.10±0.39%, and (3.20±0.14)×10$^3$ MPa, respectively.

Calculation of $M_n$ from Phthalic Anhydride-Capped PEI Polymers

Because amines can adhere to chromatography columns, the amine-terminated PEI oligomer was end-capped with phthalic anhydride (PA), as shown in Scheme 4, to allow SEC analysis and confirmation of the molecular weights that were characterized by $^1$H NMR spectroscopy.

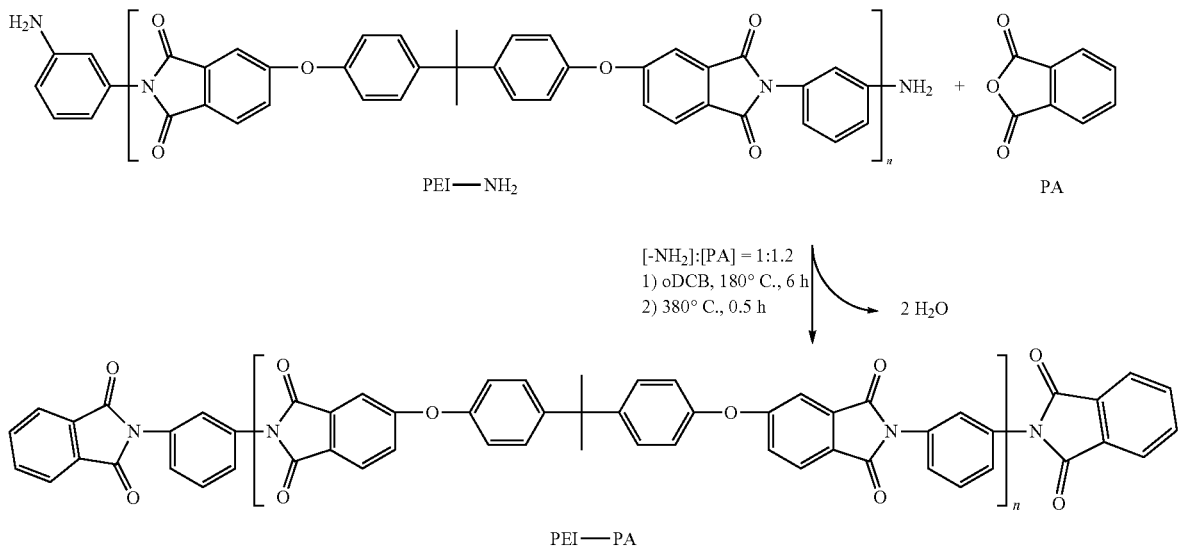

Scheme 4.

An exemplary reaction of 2k-PEI-NH$_2$ oligomer with PA is as follows. A 500 mL three-neck round-bottomed flask, equipped with an overhead stirring-rod, a Dean-Stark trap, and a nitrogen inlet, was charged with 2k-PEI-NH$_2$ (5.700 g, 1.839 mmol), PA (0.654 g, 4.41 mmol), and 60 mL ortho-dichlorobenzene (o-DCB) and purged with N$_2$. The subsequent slurry was heated to 180° C. and stirred for 6 h, then heated to 380° C. in a metal bath with a constant N$_2$ purge for another 0.5 h. The product was then dissolved in CHCl$_3$ and precipitated into MeOH. The precipitate was filtered and washed with MeOH three times, and dried in vacuo at 180° C. for 8 h.

As evidence in the $^1$H NMR spectra (FIGS. 8 and 9), the peaks representing the amine end groups in the PEI-NH$_2$ oligomer disappeared after endcapping with PA. Furthermore, new characteristic PA peaks (labeled as p and q) appeared in the $^1$H NMR spectra and had integral areas that were close to that of the integral area of the peak labeled as i in the $^1$H NMR spectra of the PEI-NH$_2$ oligomer. These show that the PEI-NH$_2$ oligomer was amine-terminated, as determined both qualitatively and quantitatively.

Figure 8:
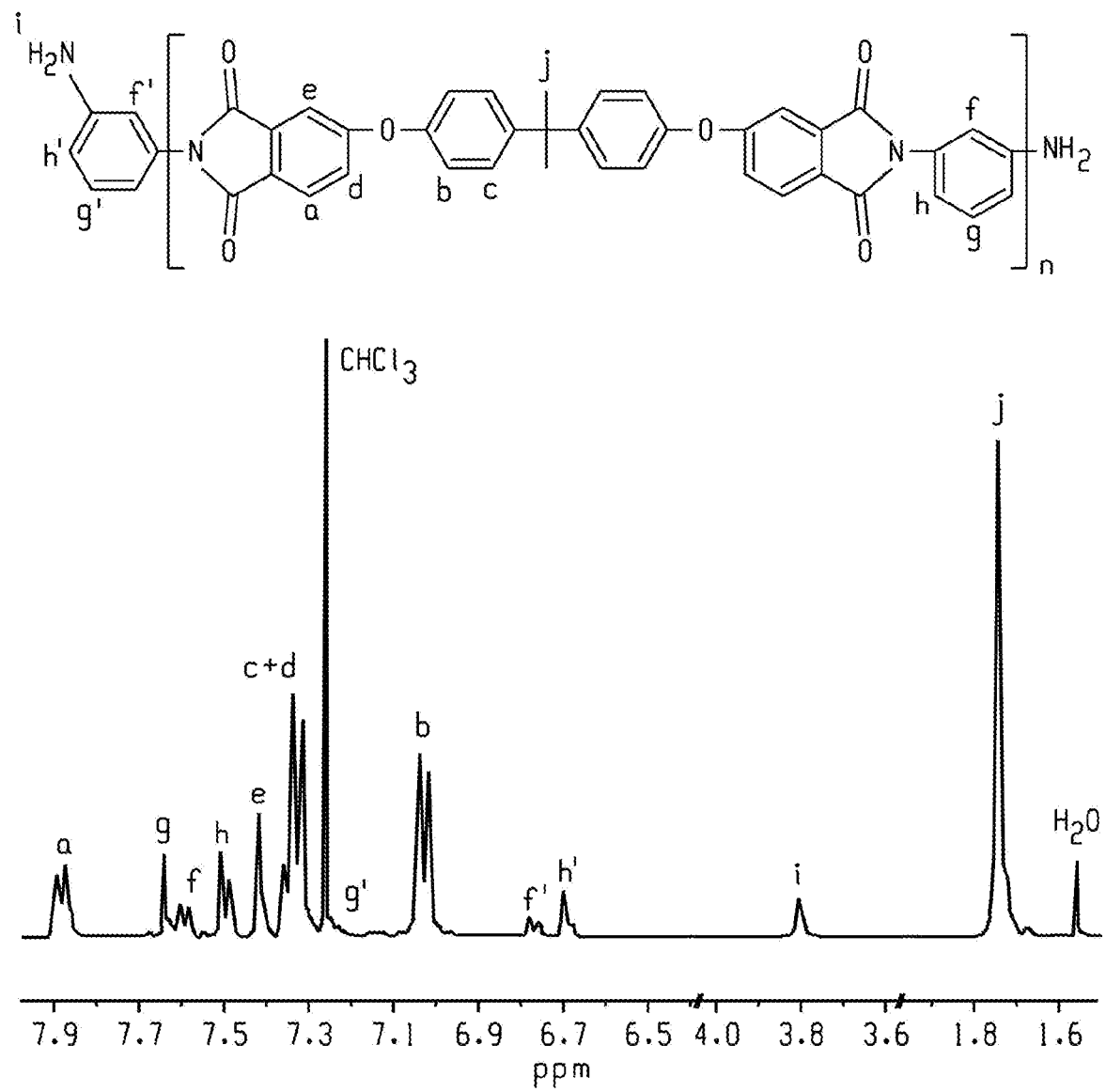
FIG. 8 is a graph of intensity (au) versus chemical shift (ppm) and shows a $^1$H NMR spectrum of 2k-PEI-NH$_2$ in CDCl$_3$ according to an embodiment.
Figure 9:
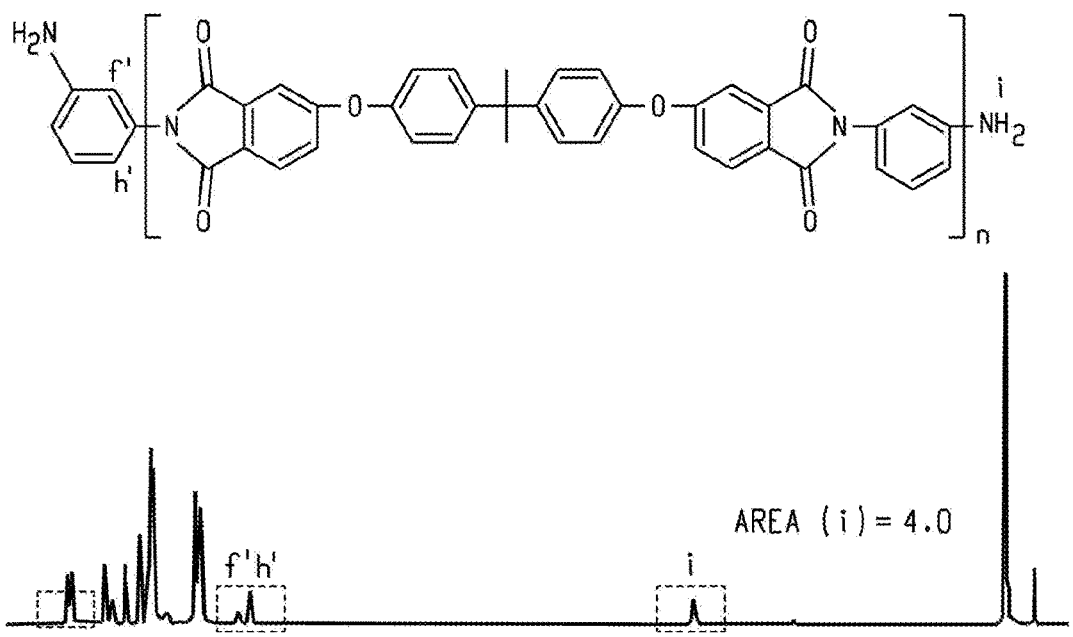
FIG. 9 shows $^1$H NMR spectra of 2k-PEI-NH$_2$ and 2k-PEI-PA according to an embodiment.
Figure 9:
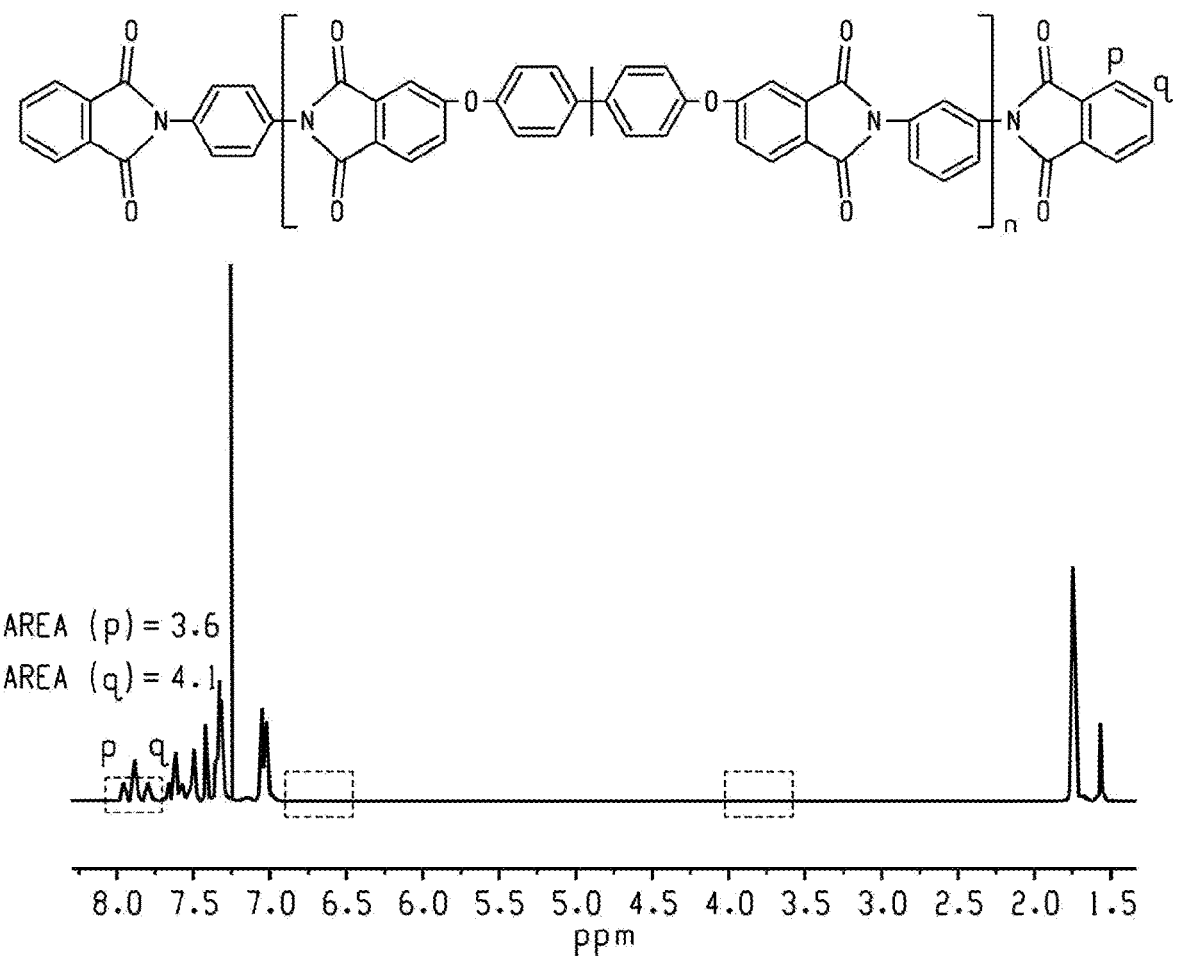

The $M_n$ and the degree of polymerization (n) of the PEI-NH$_2$ oligomer was calculated using Equations 2 and 3, and was based on the integral areas of peaks i and j as shown in FIG. 8. In particular, as shown in FIG. 9, resonance peaks i, f', and h' disappeared and new peaks p and q appeared after reacting the PEI-NH$_2$ oligomer with PA.

$$n = \frac{\text{\# of repeating units}}{\text{\# of chains}} = \frac{\text{Area}(j)/6}{\text{Area}(i)/4} \quad \text{Eq. 2}$$

$$M_n = M_{repeating\ unit} \cdot n + M_{end\ group} = (592.61n + 108.14)\,\text{g} \cdot \text{mol}^{-1} \quad \text{Eq. 3}$$

The number of repeating units in the PEI backbone was calculated by normalizing peak j by a factor of 6, since each repeating unit includes the six hydrogens of the methyl groups of BPADA. Similarly, the number of chains was normalized by a factor of 4, since each chain has the found hydrogens of the amine end groups.

Conversion from PEI-NH$_2$ to PEI-UPy

Figure 10:
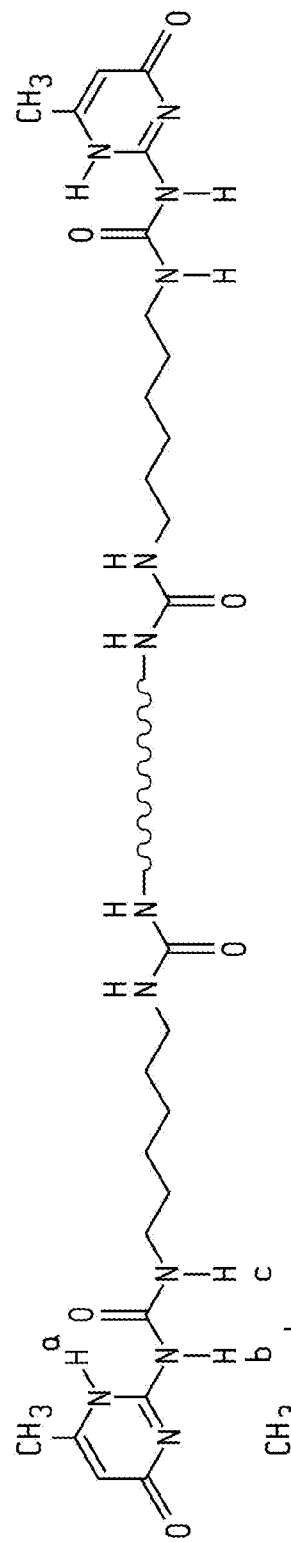
FIG. 10 shows stacked of $^1$H NMR spectra of (a) 4k-PEI-NH$_2$, (b) UPy-synthon, (c) 4k-PEI-UPy after reacting 4k-PEI-NH$_2$ with excessive UPy-synthon, (d) 4k-PEI-UPy wherein each Z' is independently the same or different, and is a substituted or unsubstituted straight or branched chain C$_{1-10}$ alkyl, each R$^1$ is independently the same or different, and is a substituted or unsubstituted straight or branched chain C$_{1-20}$ alkylene, substituted or unsubstituted C$_{2-20}$ alkenylene, substituted or unsubstituted C$_{3-8}$ cycloalkylene, or substituted or unsubstituted C$_{6-18}$ arylene, each V is independently the same or different, and is a substituted or unsubstituted tetravalent C$_{4-40}$ hydrocarbon group, each R is independently the same or different, and is a substituted or after adding silica gel to remove residual UPy-synthon, and (e) 4k-PEI-UPy after precipitation in MeOH according to an embodiment.
Figure 10:
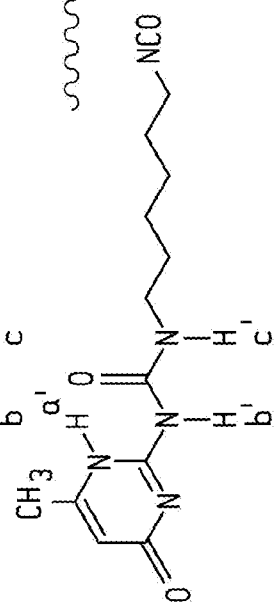
Figure 10:
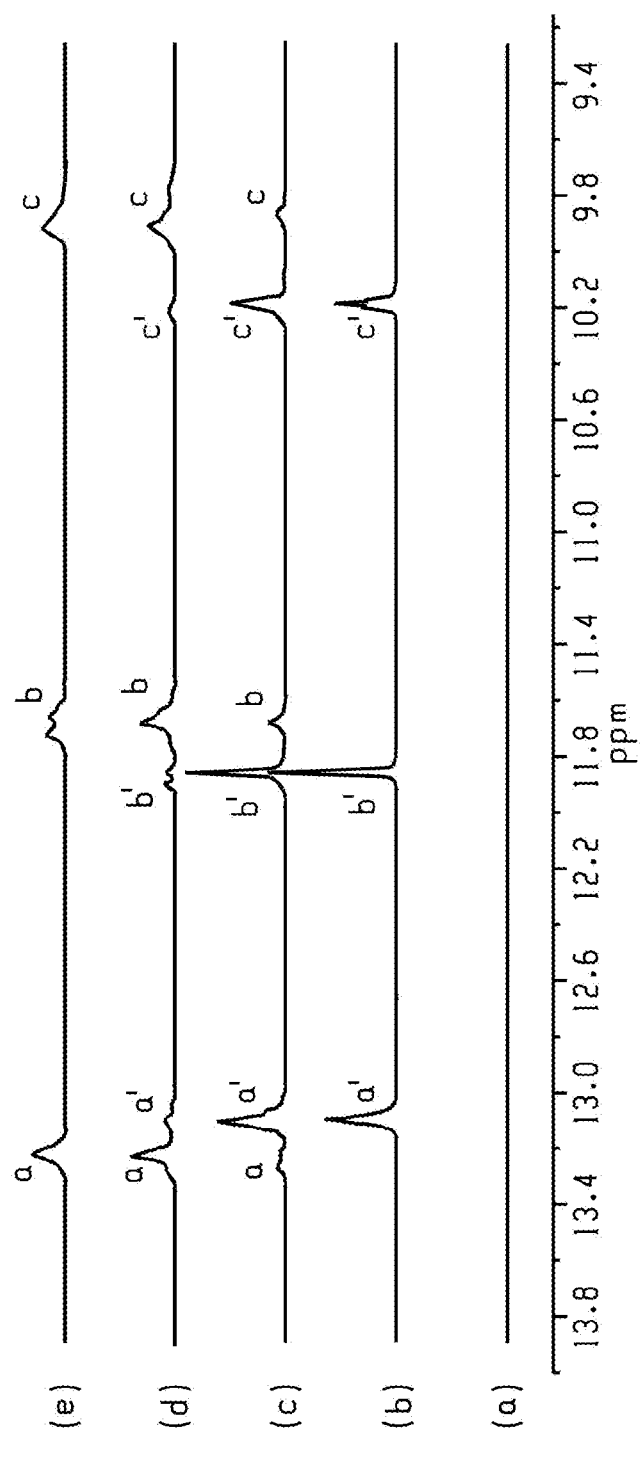

The reaction of 4k-PEI-NH$_2$ and the UPy-synthon was selected as an example to demonstrate the evolution from PEI-NH$_2$ to PEI-UPy. As shown in FIG. 10, $^1$H NMR spectra confirmed the components in each step. It is noteworthy that the three characteristic UPy peaks at 13.4-9.8 ppm shifted after incorporation of UPy. More importantly, no free UPy-synthon existed after silica gel addition and precipitation into MeOH, showing the conversion from PEI-NH$_2$ to PEI-UPy.

Calculation of the Conversion from PEI-NH$_2$ to PEI-UPy

Figure 11:
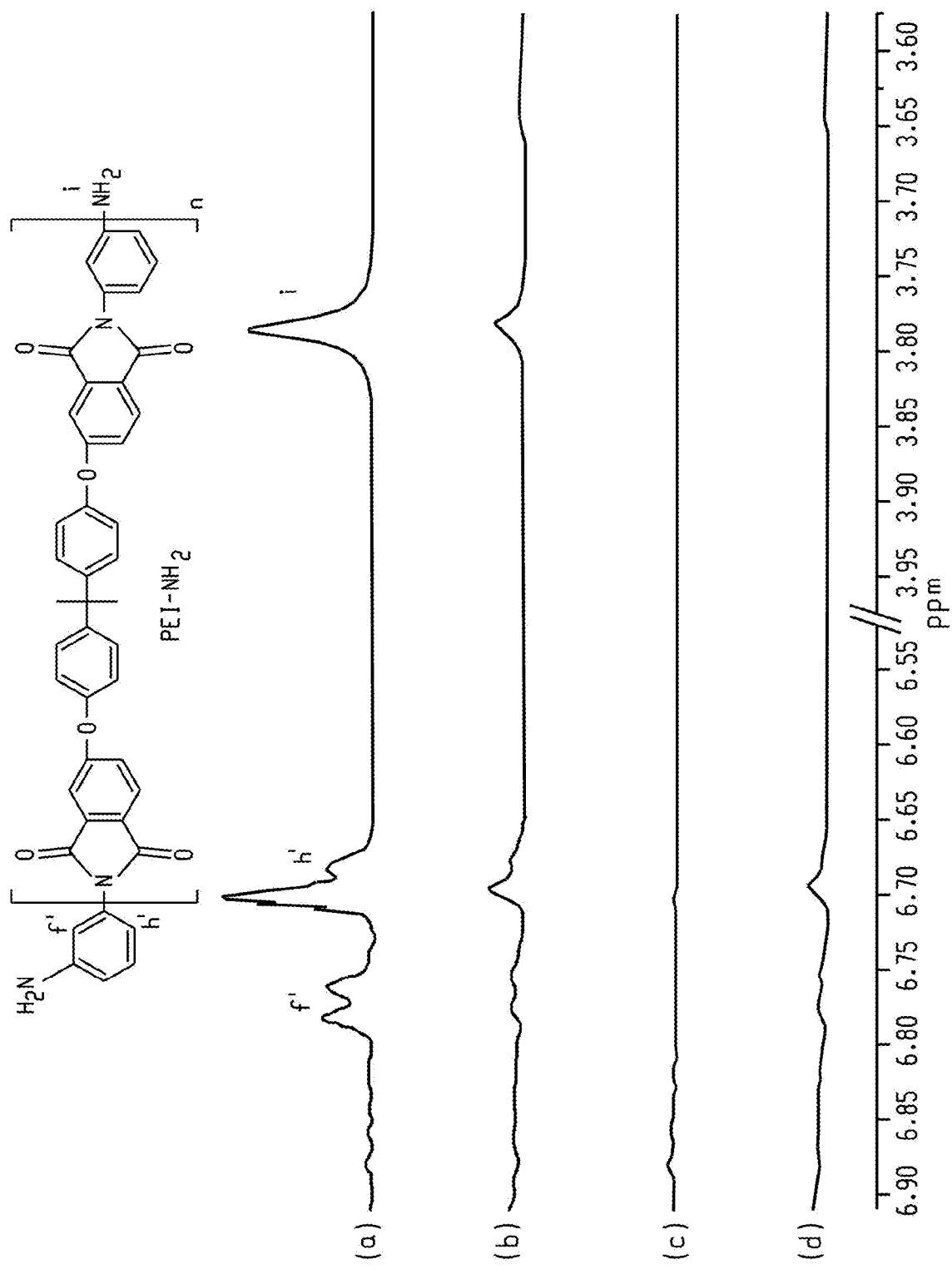
FIG. 11 shows stacked $^1$H NMR spectra of (a) 2k-PEI-NH$_2$, (b) 2k-PEI-UPy with residual 2k-PEI-NH$_2$, (c) pure 2k-PEI-PA, and (d) the 2k-PEI-UPy reaction product with PA according to an embodiment.

By reacting PA with residual PEI-NH$_2$ oligomer in the PEI-UPy oligomer product and determining the amount of resulting PEI-PA oligomer, the conversion from PEI-NH$_2$ oligomer to PEI-UPy oligomer can be calculated. For example, to determine the conversion of 2k-PEI-NH$_2$ oligomer to 2k-PEI-UPy oligomer, a 100-mL two-neck round-bottomed flask equipped with a reflux condenser and a nitrogen inlet was charged with as-synthesized 2k-PEI-UPy (0.620 g, 0.168 mmol), PA (0.030 g, 0.202 mmol), and 30 mL CHCl$_3$, and then purged with N$_2$. The subsequent slurry was heated at 60° C. for 6 h under constant stirring. The product was recovered by precipitating into MeOH. The precipitate was filtered, washed with MeOH several times, and dried in vacuo at 180° C. for 8 h. The amount of PA was calculated based on an assumption of 50% conversion from 2k-PEI-NH$_2$ oligomer to 2k-PEI-UPy oligomer. Washing the precipitate several times with MeOH will eliminate most of the PA. Neither the reaction mixture nor the precipitate was heated above 250° C. to minimize degradation of 2k-PEI-UPy oligomer. Equation 4 was used to calculate the remaining molar fraction of 2k-PEI-NH$_2$ oligomer using the integral areas of peak h' (FIG. 11).

$$\text{Conversion (NH}_2 \text{ to } UPy) = \left[ 1 - \frac{\text{Area}(h', II) - \text{Area}(h', IV)}{\text{Area}(h', I) - \text{Area}(h', III)} \right] \times 100\% \quad \text{Eq. 4}$$

Alternatively, due to the high viscosity of the reaction slurry during the reaction of PEI-NH$_2$ oligomer with the UPy-synthon, the conversion of —NH$_2$ to —UPy was not complete, indicated by the residual —NH$_2$ peaks in $^1$H NMR spectra. Thus, the conversion could be calculated by the following Equation 5, which utilized the integral areas of the amine peak (i) in FIG. 11 after the spectra were normalized to the methyl groups in PEI backbone.

$$\text{Conversion (NH}_2 \text{ to } UPy) = \left[ 1 - \frac{\text{Area}(i, PEI - UPy)}{\text{Area}(i, PEI - NH_2)} \right] \times 100\% \quad \text{Eq. 5}$$

Synthesis of PEI-U-Hex

To clarify whether the improved mechanical strength of 8k-PEI-UPy is from the UPy moieties, or from the urea linkage, or both, PEIs terminated with urea bonds and flexible hexyl chains (PEI-U-Hex) were synthesized as another set of reference polymers. The PEI-U-Hex oligomer was prepared by reacting the PEI-NH$_2$ oligomer with an excess of hexyl isocyanate (Scheme 5).

Scheme 5.

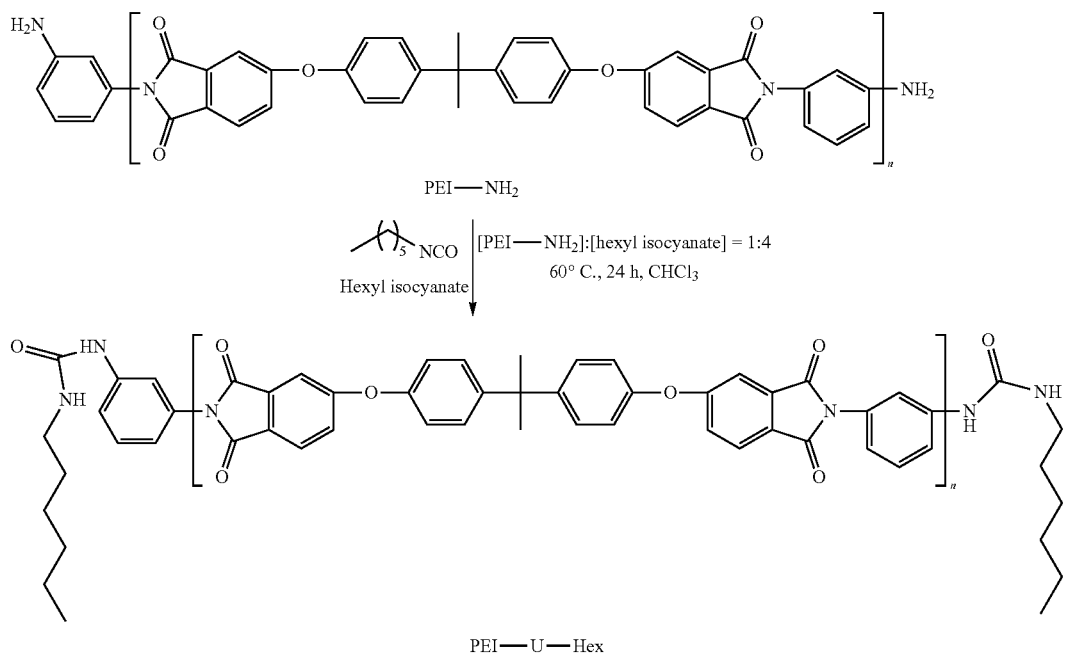

The synthesis is as follows. A flame dried, $N_2$ purged 100 mL round-bottomed flask was charged with 2k-PEI-$NH_2$ ($M_n$=3,100 g/mol, 3.100 g, 1 mmol), hexyl isocyanate (0.509 g, 4 mmol), and $CHCl_3$ (30 mL), and then purged with $N_2$. The solution was stirred at 60° C. for 24 h. Subsequently, the solution was precipitated in MeOH. The precipitate was filtered and washed with MeOH three times, and dried in vacuo at 180° C. for 6 h to provide 2k-PEI-U-Hex. A similar procedure was followed to prepare the corresponding 6k-, 4k-, and 2k-PEI-U-Hex oligomers.

Table 4 shows a summary of $T_g$ for the PEI-U-Hex oligomers and comparisons of the change in $T_g$ ($\Delta T_g$) relative to the PEI-$NH_2$ oligomers for the PEI-U-Hex and PEI-UPy oligomers.

TABLE 4

| Sample | $T_g$ (° C.) X = U-Hex | $\Delta T_g$ (° C.) X = U-Hex[a] | $\Delta T_g$ (° C.) X = UPy[b] |
| --- | --- | --- | --- |
| 8k-PEI-X | 199 | 0 | 10 |
| 6k-PEI-X | 190 | 0 | 11 |
| 4k-PEI-X | 195 | −9 | 13 |
| 2k-PEI-X | 185 | −6 | 20 |

[a,b] $\Delta T_g$ (° C.) was calculated as $T_g$ (PEI-X, ° C.) − $T_g$ (PEI-$NH_2$, ° C.), X = U-Hex or UPy.

Table 5 shows a summary of viscosity among PEI-$NH_2$, PEI-U-Hex, and PEI-UPy oligomers.

TABLE 5

| Sample | η (cP) |
| --- | --- |
| 8k-PEI-UPy | 2058 |
| 8k-PEI-U-Hex | 41.99 |
| 8k-PEI-$NH_2$ | 23.68 |
| $CHCl_3$ | 1.23 |

These results indicated that the increase in chain interactions is a result of the presence of UPy groups rather than the urea linkage.

Figure 12:
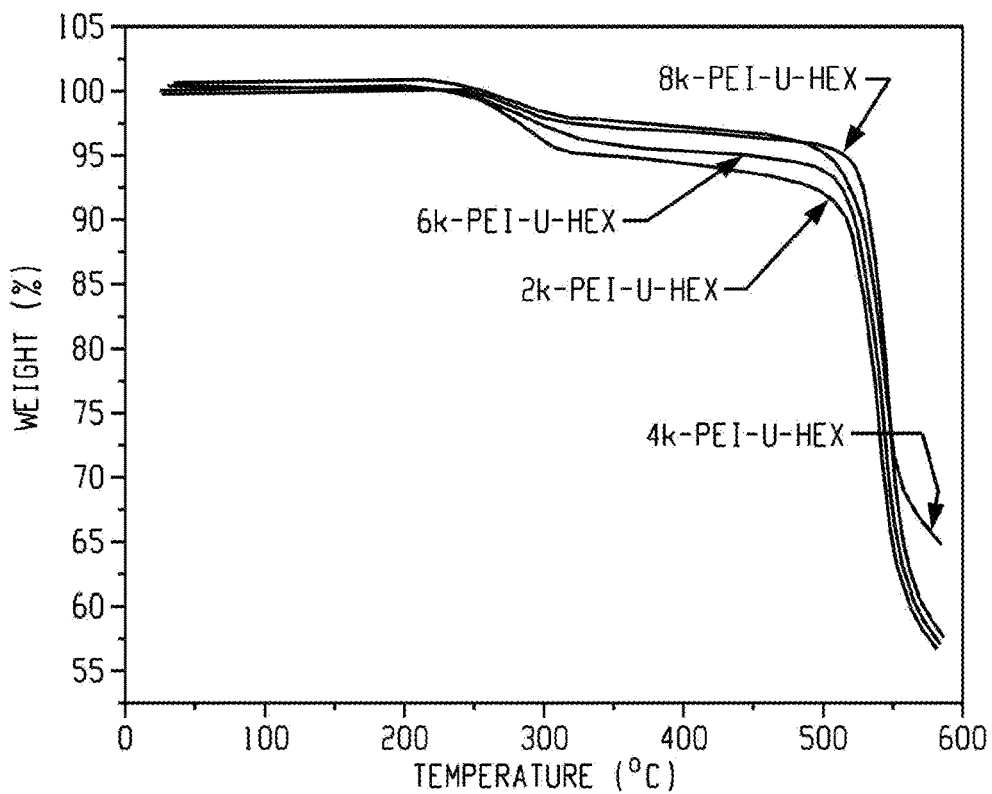
FIG. 12 is a graph of weight (%) versus temperature (° C.) and shows TGA thermograms displaying thermal stability of PEI-U-Hex oligomers according to an embodiment.
Figure 13:
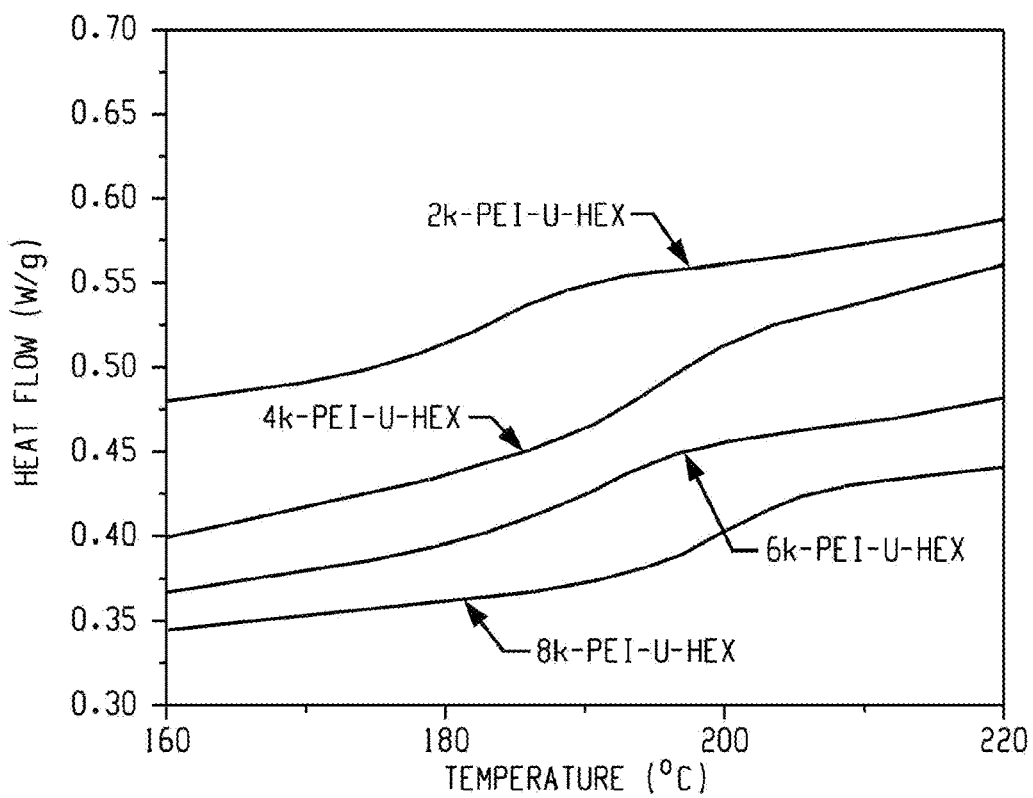
FIG. 13 is a graph of relative heat flow (au) versus temperature (° C.) and shows DSC traces of PEI-U-Hex oligomers according to an embodiment.

TGA showed the PEI-U-Hex oligomers degraded at temperatures above 240° C. (FIG. 12), which were similar to the first degradation stage for the PEI-UPy oligomers. However, the scission of covalent bonds most probably occurred at urea linkages in the PEI-U-Hex oligomers, which is different from the degradation mechanism of the PEI-UPy oligomers. DSC revealed the increasing $T_g$ with increasing molecular weight of the PEI-U-Hex oligomers (FIG. 13). DSC further revealed that the $T_g$ did not change or even decreased after formation of PEI-U-Hex oligomers compared to that of the PEI-$NH_2$ oligomer counterparts, probably owing to the incorporation of flexible alkyl chains probably.

Synthesis of PEI-Ur from PEI-$NH_2$ and Benzoyl Chloride

An exemplary reaction of 8k-PEI-$NH_2$ with benzoyl chloride is describe. A 100 mL two-neck round-bottomed flask, equipped a reflux condenser, was charged with 8k-PEI-$NH_2$ (4.000 g, 0.500 mmol), triethylamine (0.145 mL, 0.726 g/mL, 1.04 mmol), and 20 mL $CHCl_3$, and then purged with $N_2$. The flask was cooled in an ice-bath, and then benzoyl chloride (0.12 mL, 1.21 g/mL, 1.03 mmol) was added dropwise. The subsequent solution was heated at 60° C. and then refluxed for 24 h. The solution was then precipitated into MeOH. The precipitate was filtered and washed with MeOH three times, and dried in vacuo at 180° C. for 8 h to provide the 8k-PEI-Ur oligomer. A similar procedure was followed to prepare the corresponding 6k-, 4k-, and 2k-PEI-Ur oligomers.

Figure 14:
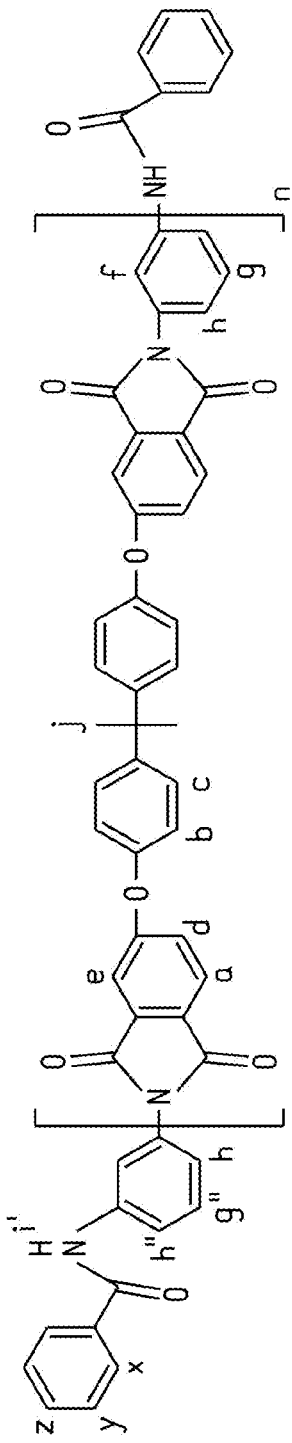
FIG. 14 is a graph of intensity (au) versus chemical shift (ppm) and shows a $^1$H NMR spectrum of a PEI-Ur oligomer according to an embodiment.
Figure 14:
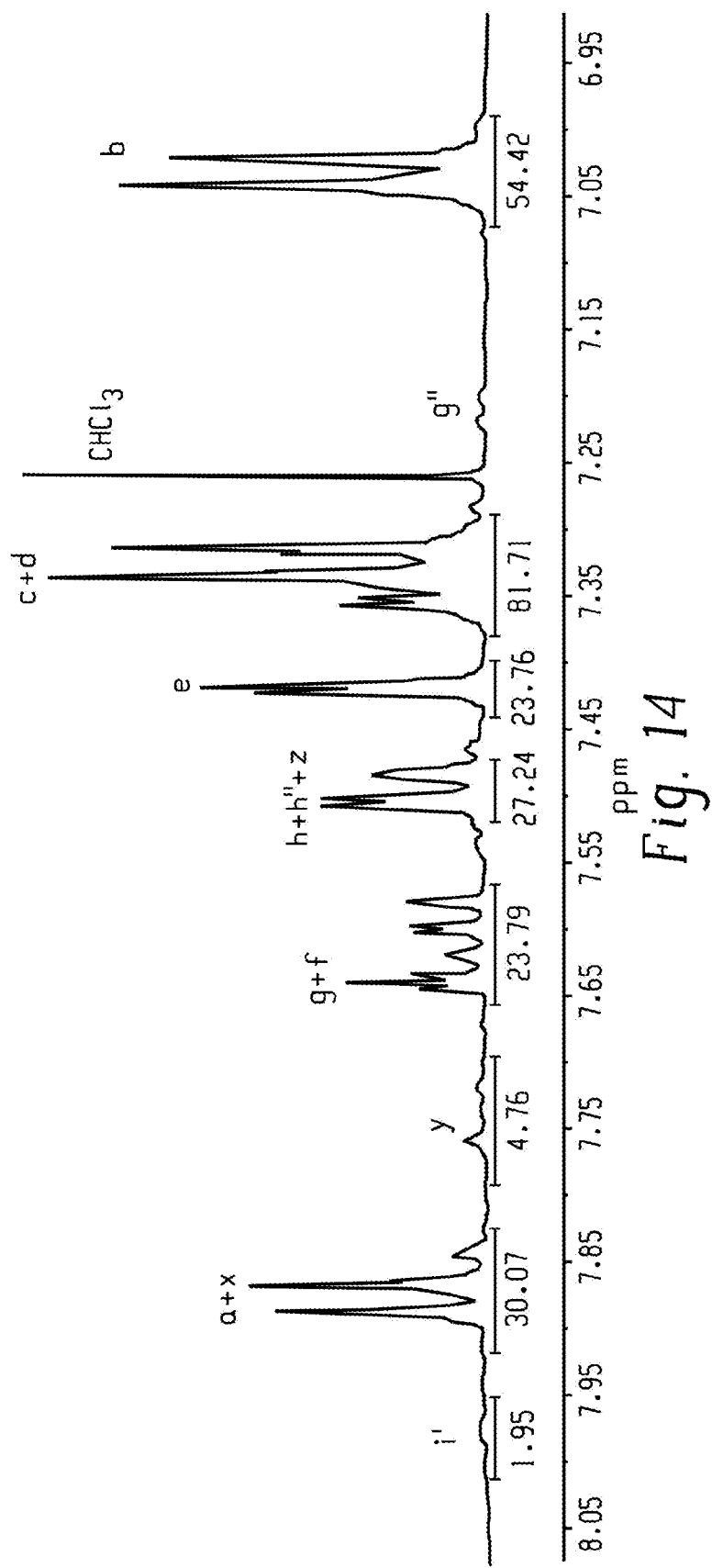
Figure 15:
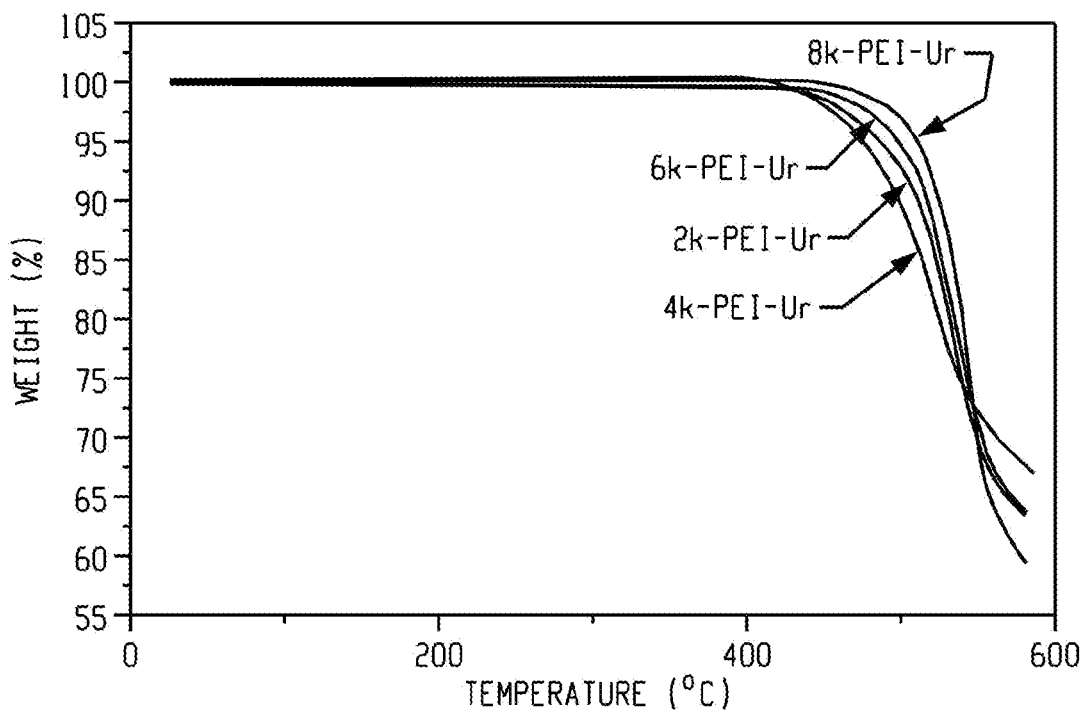
FIG. 15 is a graph of weight (%) versus temperature (° C.) and shows TGA thermograms displaying thermal stability of PEI-Ur oligomers according to an embodiment.
Figure 16:
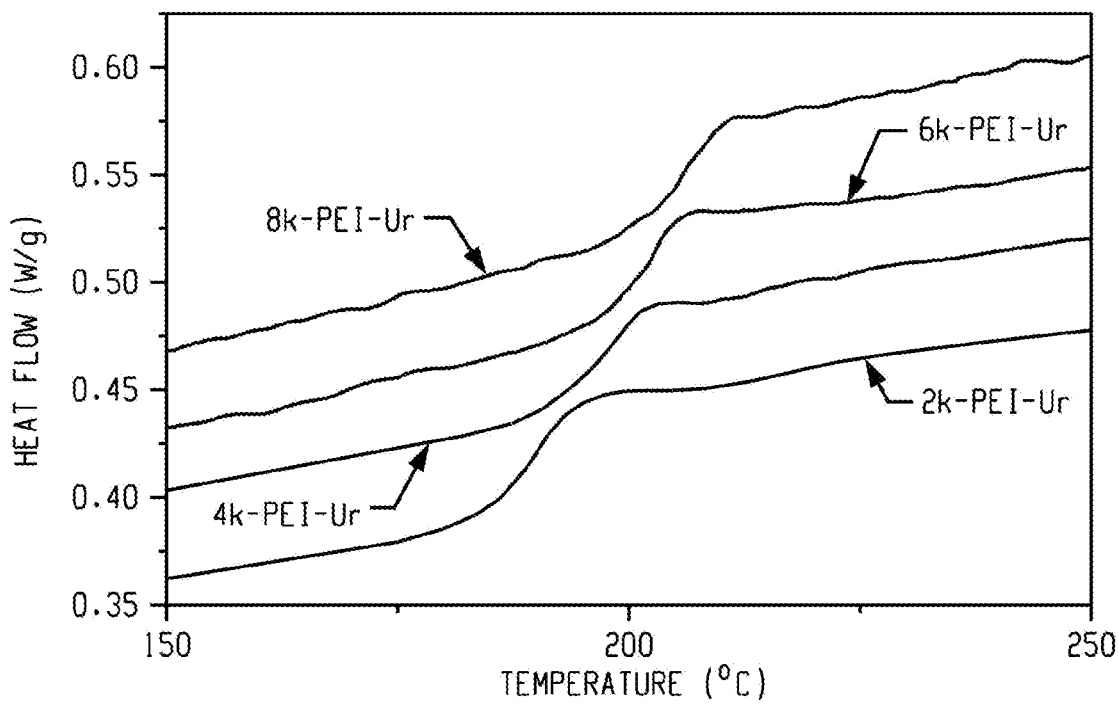
FIG. 16 is a graph of intensity (au) versus chemical shift (ppm) and shows DSC traces of PEI-Ur oligomers according to an embodiment.
Figure 17:
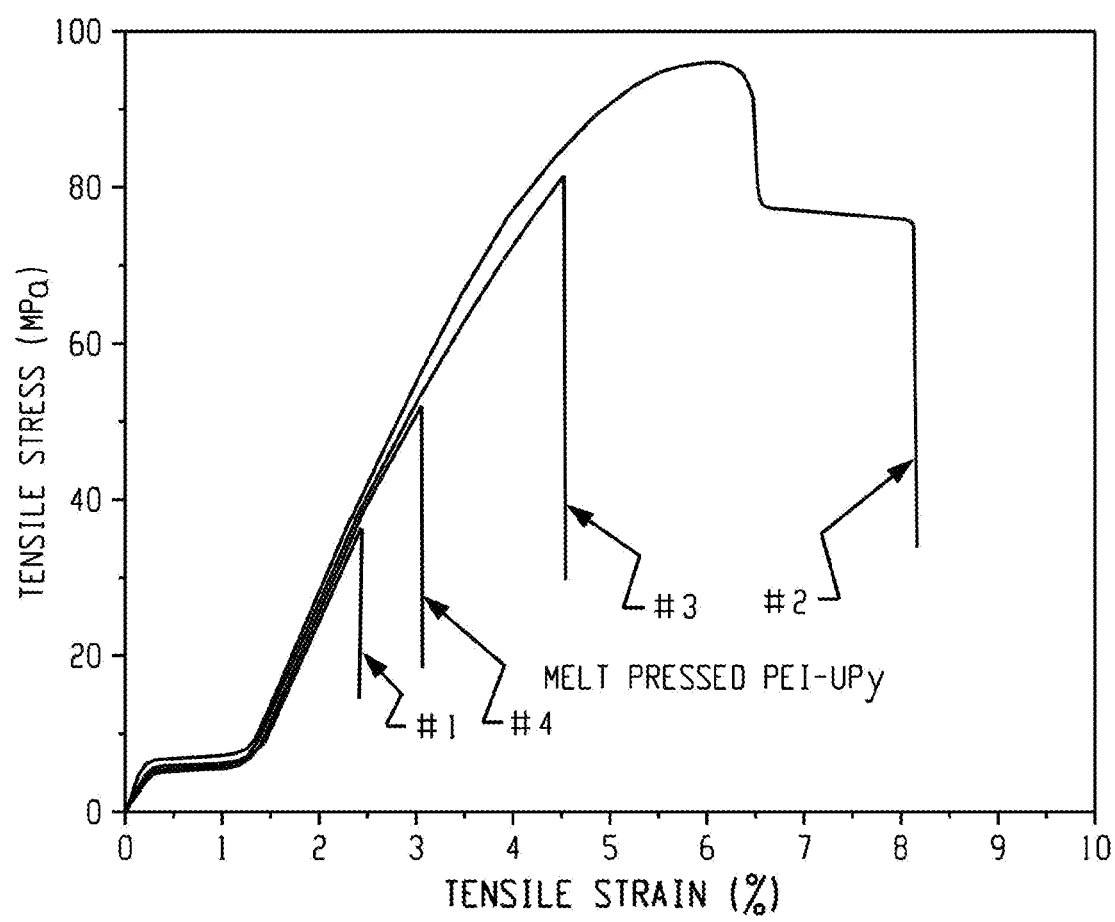
FIG. 17 is a graph of tensile stress (MPa) versus tensile strain (%) of melt pressed 8k-PEI-UPy oligomer films according to an embodiment.

As evidence in the $^1$H NMR spectra shown in FIG. 14, the peaks representing the amine end groups in PEI-$NH_2$ disappeared completely after endcapping with benzoyl chloride. Additionally, TGA elucidated that the PEI-Ur oligomers were thermally stable up to 500° C. (FIG. 15). Furthermore, DSC showed $T_g$ increased monotonically with increments in $M_n$ (FIG. 16). Endcapping with benzoyl chloride at the terminal ends of PEI-$NH_2$ led to an increase in $T_g$, although the extent of increase was not as large as from endcapping with UPy (Table 6).

TABLE 6

| $T_g$ (° C.) | PEI-$NH_2$ | PEI-Ur | PEI-UPy |
| --- | --- | --- | --- |
| 2k | 185 | 190 (+5) | 205 (+20) |
| 4k | 195 | 198 (+3) | 208 (+13) |
| 6k | 199 | 201 (+2) | 210 (+11) |
| 8k | 205 | 206 (+1) | 215 (+10) |

Melt Processing

The 8k-PEI-UPy oligomer films were hot-pressed between two Kapton sheets at 230° C. using two 0.254-mm-thick shims to control the film thickness. A mold releasing agent (provided by REXCO) was applied on the Kapton sheets to prevent the polymers from sticking. The polymer films were hot-pressed at a force of 10 tons for 1 hour. After pressing, the "sandwich" (8k-PEI-UPy film+Kapton sheets) was placed in air at room temperature for cooling.

The mechanical properties of melt processed 8k-PEI-UPy oligomer films are shown in FIG. 15. The 8k-PEI-UPy oligomer films had a tensile strength of 66.7±26.8 MPa, a maximum elongation of 3.5±2.5%, and a Young's modulus of $(2.87±0.1)×10^3$ MPa. These results showed that maximum elongation was improved by melt processing as compared with the solution-cast 8k-PEI-UPy oligomer films.

This disclosure is further illustrated by the following embodiments.

Embodiment 1

A ureido-pyrimidinone oligomer having the formula

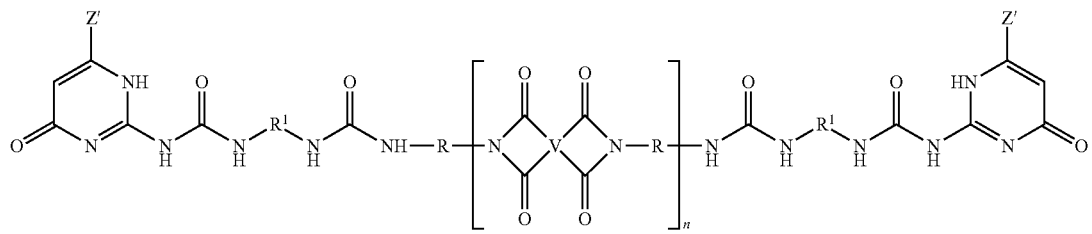

wherein each Z' is independently the same or different, and is a substituted or unsubstituted straight or branched chain $C_{1-10}$ alkyl, each $R^1$ is independently the same or different, and is a substituted or unsubstituted straight or branched chain $C_{1-20}$ alkylene, substituted or unsubstituted $C_{2-20}$ alkenylene, substituted or unsubstituted $C_3$ s cycloalkylene, or substituted or unsubstituted $C_{6-18}$ arylene, each V is independently the same or different, and is a substituted or unsubstituted tetravalent $C_{4-40}$ hydrocarbon group, each R is independently the same or different, and is a substituted or unsubstituted $C_{1-24}$ divalent hydrocarbon group; and n has an average value of 2 to 50, preferably 3 to 40, more preferably 5 to 30.

Embodiment 2

The oligomer of embodiment 1, wherein Z' is an unsubstituted $C_{1-3}$ alkyl, and $R^1$ is a straight chain $C_3$ 10 alkylene.

Embodiment 3

The oligomer of embodiment 2, wherein Z' is methyl and $R^1$ is n-hexylene.

Embodiment 4

The oligomer of any one or more of embodiments 1 to 3, wherein V is a substituted or unsubstituted $C_{6-20}$ aromatic hydrocarbon group.

Embodiment 5

The oligomer of any one or more of embodiments 1 to 4, wherein V is

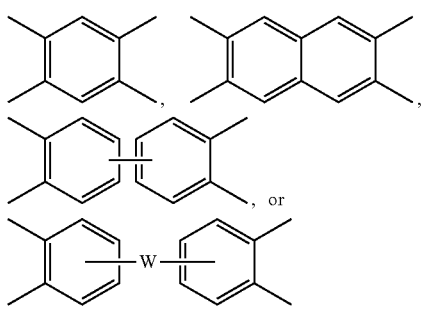

wherein W is —O—, —S—, —C(O)—, —SO$_2$—, —SO—, —P($R^a$)(═O)— wherein $R^a$ is a $C_{1-8}$ alkyl or $C_{6-12}$ aryl, —C$_y$H$_{2y}$— wherein y is an integer from 1 to 5 or a halogenated derivative thereof, or a group of the formula —O—Z—O— wherein Z is a substituted or unsubstituted aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, provided that the valence of Z is not exceeded.

Embodiment 6

The oligomer of any one or more of embodiments 1 to 5, being a poly(etherimide) of the formula

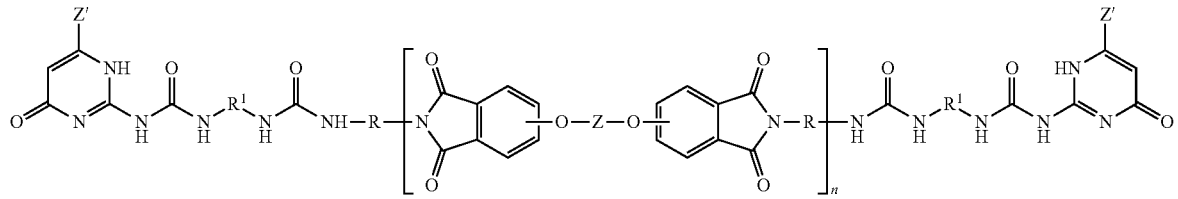

wherein each Z is independently a substituted or unsubstituted aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, provided that the valence of Z is not exceeded.

Embodiment 7

The oligomer of embodiment 6, wherein Z is a divalent group of the formula

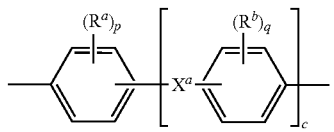

wherein each $R^a$ and $R^b$ is independently the same or different, and are a halogen atom or a monovalent $C_{1-6}$ alkyl group, p and q are each 0 to 4; c is 0 to 4; and each $X^a$ is independently the same or different, and is a single bond, —O—, —S—, —S(O)—, —S(O)$_2$—, —C(O)—, or a $C_{1-18}$ hydrocarbon group.

Embodiment 8

The oligomer of embodiment 7, wherein Z is a divalent group of the formula

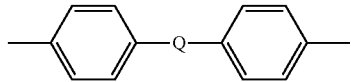

wherein Q is —O—, —S—, —C(O)—, —SO$_2$—, —SO—, or —C$_y$H$_{2y}$— wherein y is an integer from 1 to 5 or a halogenated derivative thereof.

Embodiment 9

The oligomer of any one or more of embodiments 1 to 8, wherein R is a substituted or unsubstituted $C_{6-24}$ arylene group, a substituted or unsubstituted straight or branched chain $C_{1-20}$ alkylene group, or a substituted or unsubstituted $C_{3-8}$ cycloalkylene group.

Embodiment 10

The oligomer of embodiment 9, wherein R is divalent group of the formula

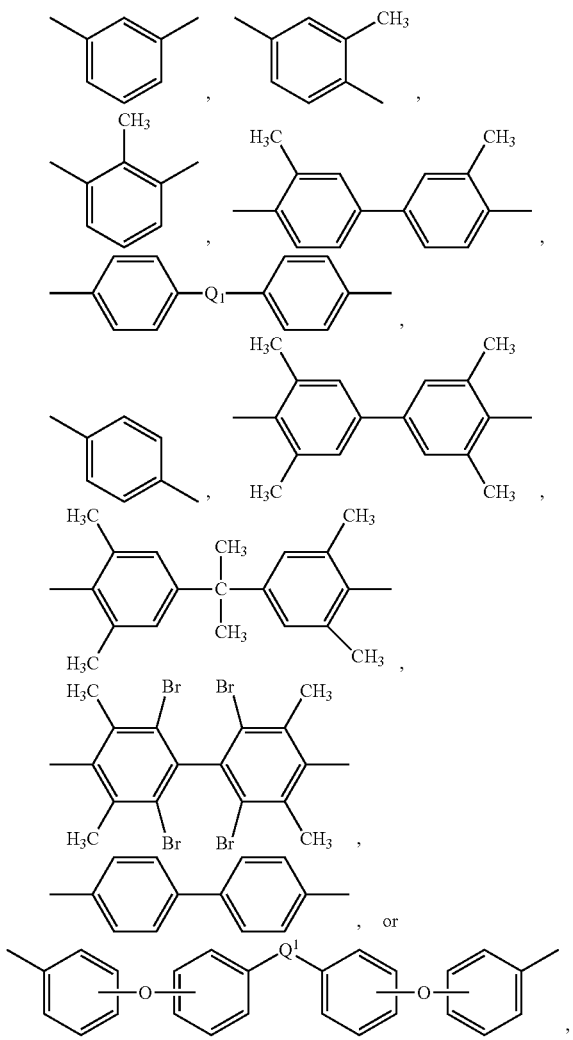

wherein $Q^1$ is —O—, —S—, —C(O)—, —SO$_2$—, —SO—, —P(R$^a$)(O)— wherein R$^a$ is a C$_{1-8}$ alkyl or C$_{6-12}$ aryl, —C$_y$H$_{2y}$— wherein y is an integer from 1 to 5 or a halogenated derivative thereof, or —(C$_6$H$_{10}$)$_z$— wherein z is an integer from 1 to 4.

Embodiment 11

The oligomer of embodiment 10, wherein R is m-phenylene, p-phenylene, bis(4,4'-phenylene)sulfone, bis(3,4'-phenylene)sulfone, or bis(3,3'-phenylene)sulfone.

Embodiment 12

A method for producing the ureido-pyrimidinone oligomer of any one or more of embodiments 1 to 11, the method comprising: reacting an amino-terminated oligomer of the formula

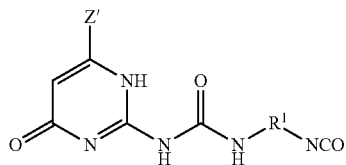

with an isocytosine of the formula

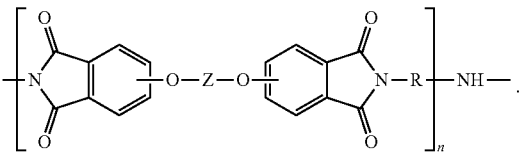

in the presence of a catalyst, under conditions effective to produce the ureido-pyrimidinone oligomer.

Embodiment 13

The method of embodiment 12, wherein the amino-terminated oligomer and the isocytosine are reacted at a mole ratio of 1:3 to 1:1.1, preferably 1:2.5 to 1:1.5.

Embodiment 14

The method of embodiment 12 or 13, wherein the reacting comprises reacting the amino-terminated oligomer and the isocytosine in a solvent at a first temperature for a first period of time to form a first intermediate mixture; adding the catalyst to the first intermediate mixture to form a second intermediate mixture; and heating the second intermediate mixture at a second temperature to provide the ureido-pyrimidinone oligomer.

Embodiment 15

The method any one or more of embodiments 12 to 14, wherein the amino-terminated oligomer is of the formula

Embodiment 16

The oligomer of any one or more of embodiments 1 to 11 or made by the method of any one or more of embodiments 12 to 15, wherein the oligomer has at least one of an intrinsic glass transition temperature of greater than or equal to 180° C., preferably 180° C. to 280° C., more preferably 200° C. to 250° C., a number average molecular weight of the ureido-pyrimidinone oligomer is 4,000 to 40,000 grams per mole, preferably 4,000 to 12,000 grams per mole, more preferably 5,000 to 10,000 grams per mole, or a Young's modulus greater than or equal to a Young's modulus of the same polyetherimide without the ureido-pyrimidinone groups, and having a molar mass of greater than 16,000 grams per mole.

Embodiment 17

An article comprising the oligomer of any one or more of embodiments 1 to 11 or made by the method of any one or more of embodiments 12 to 16.

Embodiment 18

The article of embodiment 17, wherein the article is a film, a fiber, a foam, or a molded part.

Embodiment 19

A method for the manufacture of a film, comprising solution-casting the oligomer of any one or more of embodiments 1 to 11 or made by the method of any one or more of embodiments 12 to 15.

Embodiment 20

A method for the manufacture of a film, comprising melt processing the oligomer of any one or more of embodiments 1 to 11 or made by the method of any one or more of embodiments 12 to 15

In still another embodiment, a PEI-amide oligomer is of the formula

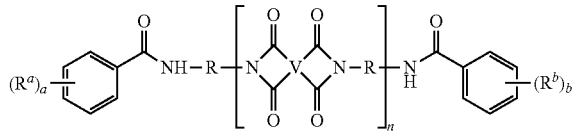

wherein each V is independently the same or different, and is a substituted or unsubstituted tetravalent $C_{4-40}$ hydrocarbon group, each R is independently the same or different, and is a substituted or unsubstituted $C_{1-20}$ divalent hydrocarbon group; each $R^a$ and $R^b$ is independently the same or different, and is a $C_{1-9}$ alkoxy, a $C_{1-9}$ haloalkoxy, a nitro, a cyano, a $C_{1-6}$ alkyl sulfonyl, a $C_{6-12}$ aryl sulfonyl, a thiol, a thiocyano, a tosyl, or a substituted or unsubstituted $C_{1-20}$ divalent hydrocarbon group, each a and b is independently 0 to 4; and n has an average value of 2 to 50, or 3 to 40, or 5 to 30.

In this embodiment, each of V and R can be the same as defined for the ureido-pyrimidinone oligomers herein.

The compositions, methods, and articles can alternatively comprise, consist of, or consist essentially of, any appropriate components or steps herein disclosed. The compositions, methods, and articles can additionally, or alternatively, be formulated to be devoid, or substantially free, of any steps, components, materials, adjuvants, or species that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combinations" is inclusive of blends, mixtures, alloys, reaction products, and the like. The terms "first," "second," and the like, do not denote any order, quantity, or importance, but rather are used to denote one element from another. The terms "a" and "an" and "the" do not denote a limitation of quantity, and are to be construed to cover both the singular and the plural, unless otherwise indicated herein or clearly contradicted by context. "Or" means "and/or" unless clearly indicated otherwise by context. Reference throughout the specification to "some embodiments," "an embodiment," and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this subject matter belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

As used herein, the term "hydrocarbyl" and "hydrocarbon" includes groups containing carbon, hydrogen, and optionally one or more heteroatoms (e.g., 1, 2, 3, or 4 atoms such as halogen, O, N, S, P, or Si). The term "alkyl" means a branched or straight chain, saturated monovalent hydrocarbon group, e.g., methyl, ethyl, n-propyl, i-propyl, n-butyl, s-butyl, t-butyl, n-pentyl, s-pentyl, n-hexyl, and s-hexyl. "Alkylene" means a straight or branched chain, saturated, divalent aliphatic hydrocarbon group (e.g., methylene ($—CH_2—$) or propylene ($—(CH_2)_3—$)). "Alkenyl" means a straight or branched chain, monovalent hydrocarbon group having at least one carbon-carbon double bond (e.g., ethenyl ($—HC=CH_2$)). "Alkenylene" means a straight or branched chain, divalent hydrocarbon group having at least one carbon-carbon double bond. "Cycloalkyl" means a non-aromatic monovalent cyclic hydrocarbon group. "Cycloalkylene" means a non-aromatic divalent cyclic hydrocarbon group. "Cycloalkenyl" means a non-aromatic monovalent group having one or more rings and one or more carbon-carbon double bonds in the ring. "Aryl" means an aromatic monovalent group containing the specified number of carbon atoms, such as phenyl. "Arylene" means an aromatic divalent group containing only carbon in the aromatic ring or rings. "Arylalkylene" means an alkyl group that has been substituted with an aryl group as defined above, with benzyl being an exemplary arylalkylene group. "Alkoxy" means an alkyl group that is linked via an oxygen (i.e., alkyl-O—), for example methoxy, ethoxy, and sec-butyloxy groups. The prefix "halo" means a group or compound including one more halogen atoms including fluoro, chloro, bromo, or iodo. A combination of different halo groups (e.g., bromo and fluoro), or only chloro groups can be present. The prefix "hetero" means that the compound or group includes at least one member that is a heteroatom (e.g., 1, 2, 3, or 4 heteroatoms), wherein the heteroatoms are each independently N, O, S, Si, or P.

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents or variables are permissible provided that the substitutions do not significantly adversely affect synthesis or use of the compound. Exemplary groups that can be present on a "substituted" position include, but are not limited to, nitro (—NO$_2$), cyano (—CN), C$_{1-6}$ alkylsulfonyl (—S(=O)$_2$-alkyl), C$_{6-12}$ arylsulfonyl (—S(=O)$_2$-aryl), thiol (—SH), thiocyano (—SCN), tosyl (CH$_3$C$_6$H$_4$SO$_2$—), halo, C$_{1-9}$ alkyl, C$_{3-12}$ cycloalkyl, C$_{2-12}$ alkenyl, C$_{5-12}$ cycloalkenyl, C$_{6-12}$ aryl, C$_{7-13}$ arylalkylene, C$_{1-9}$ alkoxy, C$_{1-9}$ haloalkoxy, C$_{4-12}$ heterocycloalkyl, or C$_{3-12}$ heteroaryl.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A ureido-pyrimidinone oligomer having the formula

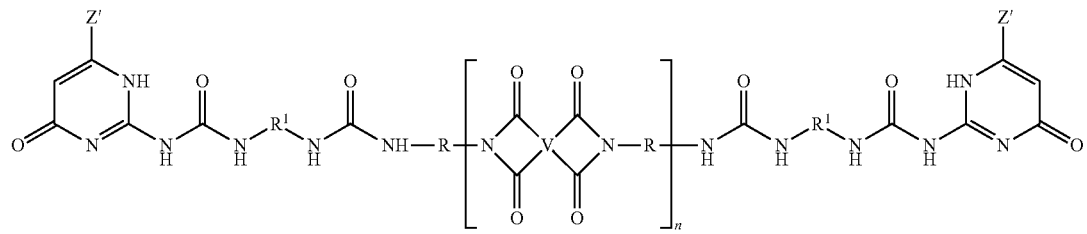

wherein
- each Z' is independently the same or different, and is a substituted or unsubstituted straight or branched chain C$_{1-10}$ alkyl,
- each R$^1$ is independently the same or different, and is a substituted or unsubstituted straight or branched chain C$_{1-20}$ alkylene, substituted or unsubstituted C$_{2-20}$ alkenylene, substituted or unsubstituted C$_{3-8}$ cycloalkylene, or substituted or unsubstituted C$_{6-18}$ arylene,
- each V is independently the same or different, and is a substituted or unsubstituted tetravalent C$_{4-40}$ hydrocarbon group,
- each R is independently the same or different, and is a substituted or unsubstituted C$_{1-24}$ divalent hydrocarbon group, and
- n has an average value of 2 to 50.

2. The oligomer of claim 1, wherein Z' is an unsubstituted C$_{1-3}$ alkyl, and R$^1$ is a straight chain C$_{3-10}$ alkylene.

3. The oligomer of claim 2, wherein Z' is methyl and R$^1$ is n-hexylene.

4. The oligomer of claim 1, wherein V is a substituted or unsubstituted C$_{6-20}$ aromatic hydrocarbon group.

5. The oligomer of claim 1, wherein V is

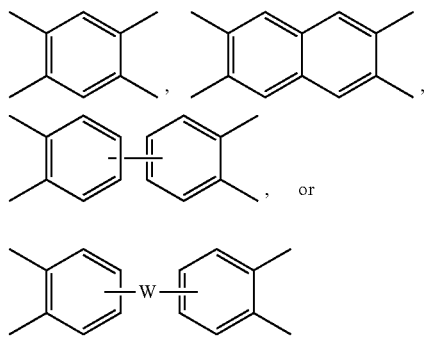

wherein W is —O—, —S—, —C(O)—, —SO$_2$—, —SO—, —P(R$^a$)(=O)— wherein R$^a$ is a C$_{1-8}$ alkyl or C$_{6-12}$ aryl, —C$_y$H$_{2y}$— wherein y is an integer from 1 to 5 or a halogenated derivative thereof, or a group of the formula —O—Z—O— wherein Z is a substituted or unsubstituted aromatic C$_{6-24}$ monocyclic or polycyclic moiety optionally substituted with 1 to 6 C$_{1-8}$ alkyl groups, 1 to 8 halogen atoms, or a combination thereof, provided that the valence of Z is not exceeded.

6. The oligomer of claim 1, being a poly(etherimide) of the formula

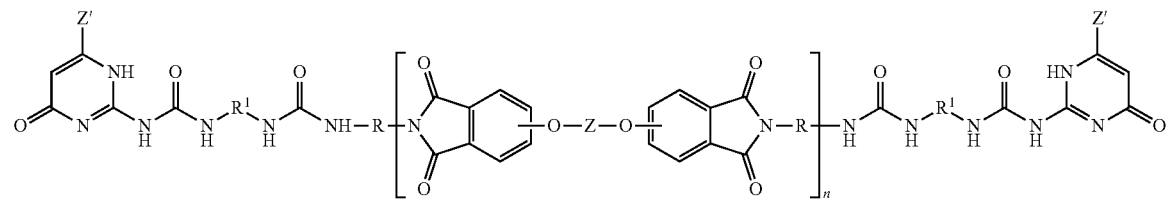

wherein each Z is independently a substituted or unsubstituted aromatic C$_{6-24}$ monocyclic or polycyclic moiety optionally substituted with 1 to 6 C$_{1-8}$ alkyl groups, 1 to 8 halogen atoms, or a combination thereof, provided that the valence of Z is not exceeded.

7. The oligomer of claim 6, wherein Z is a divalent group of the formula

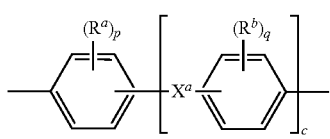

wherein
  each $R^a$ and $R^b$ is independently the same or different, and is a halogen atom or a monovalent $C_{1-6}$ alkyl group, p and q are each 0 to 4;
  c is 0 to 4; and
  each $X^a$ is independently the same or different, and is a single bond, —O—, —S—, —S(O)—, —S(O)$_2$—, —C(O)—, or a $C_{1-18}$ hydrocarbon group.

8. The oligomer of claim 7, wherein Z is a divalent group of the formula

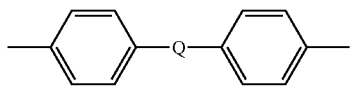

wherein Q is —O—, —S—, —C(O)—, —SO$_2$—, —SO—, or —C$_y$H$_{2y}$— wherein y is an integer from 1 to 5 or a halogenated derivative thereof.

9. The oligomer of claim 1, wherein R is a substituted or unsubstituted $C_{6-24}$ arylene group, a substituted or unsubstituted straight or branched chain $C_{1-20}$ alkylene group, or a substituted or unsubstituted $C_{3-8}$ cycloalkylene group.

10. The oligomer of claim 9, wherein R is divalent group of the formula

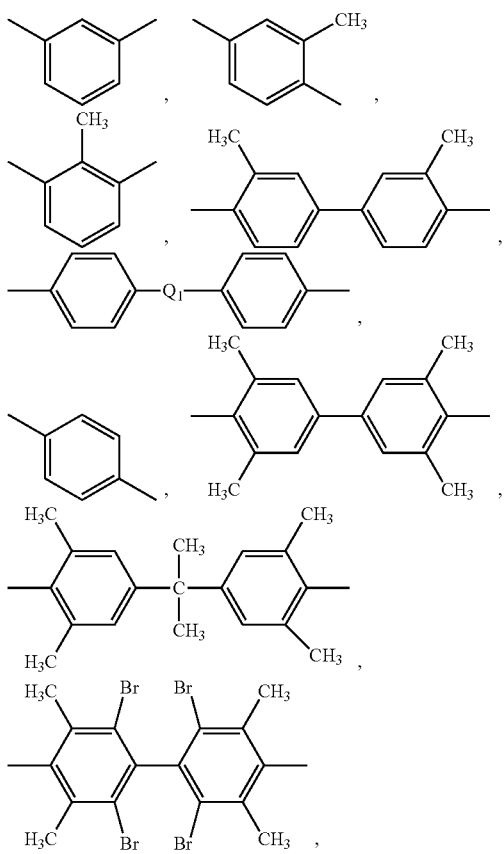

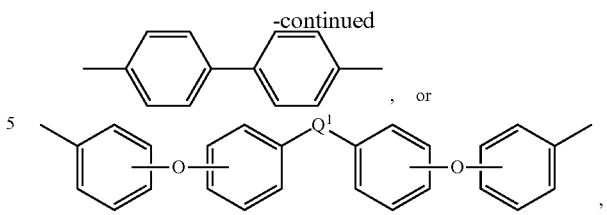

wherein $Q^1$ is —O—, —S—, —C(O)—, —SO$_2$—, —SO—, —P(R$^a$)(O)— wherein W is a $C_{1-8}$ alkyl or $C_{6-12}$ aryl, —C$_y$H$_{2y}$— wherein y is an integer from 1 to 5 or a halogenated derivative thereof, or —(C$_6$H$_{10}$)$_z$— wherein z is an integer from 1 to 4.

11. The oligomer of claim 10, wherein R is m-phenylene, p-phenylene, bis(4,4'-phenylene)sulfone, bis(3,4'-phenylene)sulfone, or bis(3,3'-phenylene)sulfone.

12. A method for producing the ureido-pyrimidinone oligomer of claim 1, the method comprising: reacting an amino-terminated oligomer of the formula

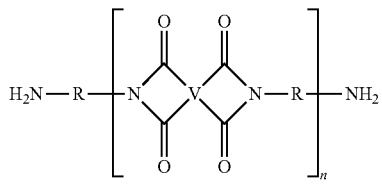

with an isocytosine of the formula

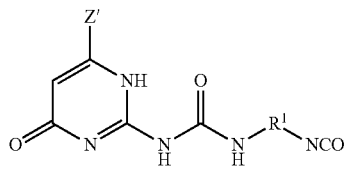

in the presence of a catalyst, under conditions effective to produce the ureido-pyrimidinone oligomer.

13. The method of claim 12, wherein the amino-terminated oligomer and the isocytosine are reacted at a mole ratio of 1:3 to 1:1.1.

14. The method of claim 12, wherein the reacting comprises
  reacting the amino-terminated oligomer and the isocytosine in a solvent at a first temperature for a first period of time to form a first intermediate mixture;
  adding the catalyst to the first intermediate mixture to form a second intermediate mixture; and
  heating the second intermediate mixture at a second temperature to provide the ureido-pyrimidinone oligomer.

15. The method of claim 12, wherein the amino-terminated oligomer is of the formula

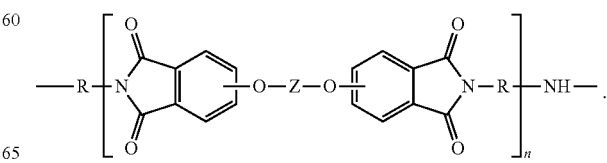

16. The oligomer of claim 1, wherein the oligomer has at least one of
   an intrinsic glass transition temperature of greater than or equal to 180° C.,
   a number average molecular weight of the ureido-pyrimidinone oligomer is 4,000 to 40,000 grams per mole, or
   a Young's modulus greater than or equal to a Young's modulus of the same polyetherimide without the ureido-pyrimidinone groups, and having a molar mass of greater than 16,000 grams per mole.

17. An article comprising the oligomer of claim 1.

18. The article of claim 17, wherein the article is a film, a fiber, a foam, or a molded part.

19. The article of claim 17, wherein the article is a film prepared by solution-casting the oligomer.

20. The article of claim 18, wherein the article is a film prepared by melt processing the oligomer.

\* \* \* \* \*